US012274786B2

(12) United States Patent
Klein et al.

(10) Patent No.: US 12,274,786 B2
(45) Date of Patent: Apr. 15, 2025

(54) SURFACE TREATMENT OF CONTACT LENS AND TREATMENT OF OCULAR DISCOMFORT BY WATER SOLUBLE POLYMERS AND LIPIDS/LIPOSOMES

(71) Applicant: Yeda Research and Development Co. Ltd., Rehovot (IL)

(72) Inventors: Jacob Klein, Rehovot (IL); Ronit Goldberg, Rehovot (IL); Jasmine Seror, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 716 days.

(21) Appl. No.: 17/406,168

(22) Filed: Aug. 19, 2021

(65) Prior Publication Data

US 2021/0378960 A1    Dec. 9, 2021

Related U.S. Application Data

(62) Division of application No. 15/319,014, filed as application No. PCT/IL2015/050605 on Jun. 15, 2015, now Pat. No. 11,883,533.

(60) Provisional application No. 62/012,379, filed on Jun. 15, 2014.

(51) Int. Cl.
| A61K 9/127 | (2006.01) |
| A61K 9/00 | (2006.01) |
| A61K 9/08 | (2006.01) |
| A61K 31/728 | (2006.01) |
| A61K 31/77 | (2006.01) |
| A61K 31/79 | (2006.01) |
| A61K 47/10 | (2017.01) |
| A61K 47/32 | (2006.01) |
| A61K 47/36 | (2006.01) |
| B65D 35/00 | (2006.01) |
| B65D 75/36 | (2006.01) |

(52) U.S. Cl.
CPC ............ *A61K 9/127* (2013.01); *A61K 9/0048* (2013.01); *A61K 9/08* (2013.01); *A61K 31/728* (2013.01); *A61K 31/77* (2013.01); *A61K 31/79* (2013.01); *A61K 47/10* (2013.01); *A61K 47/32* (2013.01); *A61K 47/36* (2013.01); *B65D 35/00* (2013.01); *B65D 75/36* (2013.01)

(58) Field of Classification Search
None
See application file for complete search history.

(56) References Cited

U.S. PATENT DOCUMENTS

| 4,613,665 A | 9/1986 | Larm |
| 4,804,539 A | 2/1989 | Guo et al. |
| 4,810,784 A | 3/1989 | Larm |
| 4,818,537 A | 4/1989 | Guo |
| 4,925,017 A | 5/1990 | Jessen |
| 5,037,677 A | 8/1991 | Halpern et al. |
| 5,336,518 A | 8/1994 | Narayanan et al. |
| 5,356,433 A | 10/1994 | Rowland et al. |
| 5,364,637 A | 11/1994 | De et al. |
| 5,403,592 A | 4/1995 | Hills |
| 5,895,645 A | 4/1999 | Dabrowski et al. |
| 5,997,517 A | 12/1999 | Whitbourne |
| 6,592,907 B2 | 7/2003 | Karagoezian |
| 6,800,298 B1 | 10/2004 | Burdick et al. |
| 6,822,016 B2 * | 11/2004 | McCabe ............... C08F 251/00 524/265 |
| 7,083,803 B2 | 8/2006 | Peyman |
| 7,638,137 B2 | 12/2009 | Chauhan et al. |
| 8,273,366 B2 | 9/2012 | Chauhan et al. |
| 10,940,111 B2 | 3/2021 | Klein |
| 2003/0165015 A1 | 9/2003 | Jahnke |
| 2004/0171740 A1 | 9/2004 | Ruberti et al. |
| 2005/0191331 A1 | 9/2005 | Hunter et al. |
| 2006/0094643 A1 * | 5/2006 | Svirkin ............... A61K 47/186 514/310 |
| 2006/0210511 A1 | 9/2006 | Stone et al. |
| 2006/0251685 A1 | 11/2006 | Yu et al. |
| 2006/0270781 A1 | 11/2006 | Ruberti et al. |
| 2007/0237803 A1 | 10/2007 | Cheng et al. |
| 2007/0292496 A1 | 12/2007 | Herrero-Vanrell et al. |
| 2009/0192478 A1 | 7/2009 | Soroudi |
| 2010/0098749 A1 | 4/2010 | Barenholz et al. |
| 2010/0098772 A1 | 4/2010 | Robinson et al. |
| 2011/0097277 A1 | 4/2011 | Jiang et al. |

(Continued)

FOREIGN PATENT DOCUMENTS

| CN | 104013491 | * | 9/2014 |
| EP | 0216453 | | 4/1987 |

(Continued)

OTHER PUBLICATIONS

Notice of Allowance Dated Jan. 12, 2023 from the Re. U.S. Appl. No. 17/190,537. (3 pages).

(Continued)

*Primary Examiner* — Brian Gulledge

(57) ABSTRACT

Formulations (e.g., solutions) comprising one or more water-soluble polymer(s), liposomes, and an aqueous carrier, are provided. The provided solutions are useful for rinsing, and/or immersing therein, a contact lens and/or in the treatment of ocular discomfort, for example, an ocular discomfort associated with a contact lens. Also provided are kits comprising the solution and a contact lens; articles-of-manufacturing comprising the solution and configured for dispending the solution; and methods utilizing the solution.

11 Claims, 4 Drawing Sheets

(56) References Cited

U.S. PATENT DOCUMENTS

| | | |
|---|---|---|
| 2011/0293699 A1 | 12/2011 | Bennett et al. |
| 2012/0064150 A1 | 3/2012 | Wisniewski et al. |
| 2012/0121694 A1 | 5/2012 | Adkins, Jr. et al. |
| 2012/0128763 A1 | 5/2012 | Maskin |
| 2012/0148667 A1 | 6/2012 | Callegaro et al. |
| 2012/0238519 A1 | 9/2012 | Matsumoto et al. |
| 2014/0099343 A1 | 4/2014 | Sullivan et al. |
| 2017/0119811 A1 | 5/2017 | Klein et al. |
| 2017/0128365 A1 | 5/2017 | Klein et al. |
| 2021/0018687 A1 | 6/2021 | Klein et al. |

FOREIGN PATENT DOCUMENTS

| | | |
|---|---|---|
| EP | 0341745 | 11/1989 |
| EP | 0138572 | 7/1990 |
| EP | 0702699 | 3/1996 |
| EP | 1095064 | 5/2001 |
| EP | 1313772 | 5/2003 |
| EP | 1339753 | 9/2003 |
| WO | WO 03/000190 | 1/2003 |
| WO | WO 2008/038292 | 4/2008 |
| WO | WO 2011/158237 | 12/2011 |
| WO | WO 2014/071132 | 5/2014 |
| WO | WO 2015/193887 | 12/2015 |
| WO | WO 2015/193888 | 12/2015 |

OTHER PUBLICATIONS

Examiner answer Appeal Brief Dated Mar. 25, 2022 from Re. U.S. Appl. No. 16/319,014. (15 pages).
Examiner's Answer Dated Mar. 25, 2022 From the Re. U.S. Appl. No. 15/319,014. (15 Pages).
Reverse Decision on Appeal Dated Jun. 27, 2023 from the Re. U.S. Appl. No. 15/319,014. (7 pages).
Advisory Action Dated Jul. 20, 2020 from the Re. U.S. Appl. No. 15/319,014. (8 pages).
Communication Pursuant to Article 94(3) EPC Dated Jan. 18, 2019 From the European Patent Office Re. Application No. 15810541.1. (4 Pages).
Communication Pursuant to Article 94(3) EPC Dated Mar. 27, 2020 From the European Patent Office Re. Application No. 15810541.1. (4 Pages).
Communication Pursuant to Article 94(3) EPC Dated Jul. 6, 2020 From the European Patent Office Re. Application No. 15810541.1. (6 Pages).
Communication Pursuant to Article 94(3) EPC Dated Jul. 11, 2019 From the European Patent Office Re. Application No. 15808959.9. (4 Pages).
Communication Pursuant to Rule 164(1) EPC [Supplementary Partial European Search Report and the European Provisional Opinion] Dated Jan. 2, 2018 From the European Patent Office Re. Application No. 15808959.9. (15 Pages).
Decision of Rejection Dated Feb. 2, 2021 From the National Intellectual Property Administration of the People's Republic of China Re. Application No. 201580043754.8. (12 Pages).
Final Official Action Dated May 7, 2021 From the Re. U.S. Appl. No. 15/319,014. (25 Pages).
Final Official Action Dated Apr. 3, 2020 from the Re. U.S. Appl. No. 15/319,005. (12 pages).
Final Official Action Dated Mar. 9, 2020 from the Re. U.S. Appl. No. 15/319,014. (12 pages).
International Preliminary Report on Patentability Dated Dec. 22, 2016 From the International Bureau of WIPO Re. Application No. PCT/IL2015/050605. (10 Pages).
International Preliminary Report on Patentability Dated Dec. 22, 2016 From the International Bureau of WIPO Re. Application No. PCT/IL2015/050606. (8 Pages).
International Search Report and the Written Opinion Dated Oct. 6, 2015 From the International Searching Authority Re. Application No. PCT/IL2015/050606.
International Search Report and the Written Opinion Dated Sep. 20, 2015 From the International Searching Authority Re. Application No. PCT/IL2015/050605.
Interview Summary Dated May 14, 2020 from the Re. U.S. Appl. No. 15/319,014. (4 pages).
Notice of Allowance Dated Oct. 15, 2020 From the Re. U.S. Appl. No. 15/319,005. (10 pages).
Notification of Office Action and Search Report Dated Feb. 2, 2019 From the National Intellectual Property Administration of the People's Republic of China Re. Application No. 201580043754.8 and Its Translation Into English. (36 Pages).
Notification of Office Action and Search Report Dated Jul. 2, 2020 From the National Intellectual Property Administration of the People's Republic of China Re. Application No. 201580043754.8 and Its Translation Into English. (34 Pages).
Notification of Office Action Dated Sep. 18, 2019 From the National Intellectual Property Administration of the People's Republic of China Re. Application No. 201580043754.8 and Its Translation Into English. (18 Pages).
Office Action Dated Feb. 13, 2019 From the Israel Patent Office Re. Application No. 249573 and Its Translation Into English. (6 Pages).
Office Action Dated May 19, 2020 From the Israel Patent Office Re. Application No. 249573 and Its Translation Into English. (13 Pages).
Official Action Dated Jun. 7, 2018 From the Re. U.S. Appl. No. 15/319,014. (25 pages).
Official Action Dated Jul. 8, 2019 From the Re. U.S. Appl. No. 15/319,014. (17 pages).
Official Action Dated Jun. 13, 2018 From the Re. U.S. Appl. No. 15/319,005. (12 pages).
Official Action Dated Apr. 17, 2019 From the Re. U.S. Appl. No. 15/319,005. (14 Pages).
Official Action Dated Sep. 18, 2018 From the Re. U.S. Appl. No. 15/319,005. (9 Pages).
Official Action Dated Oct. 19, 2017 From the Re. U.S. Appl. No. 15/319,005. (14 pages).
Official Action Dated Oct. 22, 2020 From the Re. U.S. Appl. No. 15/319,014. (26 Pages).
Official Action Dated Sep. 27, 2019 From the Re. U.S. Appl. No. 15/319,005. (8 pages).
Official Action Dated Jan. 29, 2019 From the Re. U.S. Appl. No. 15/319,014. (10 Pages).
Requisition by the Examiner Dated May 13, 2021 From the Innovation, Science and Economic Development Canada, Canadian Intellectual Property Office Re. Application No. 2,950,535. (4 Pages).
Supplementary European Search Report and the European Search Opinion Dated Apr. 18, 2018 From the European Patent Office Re. Application No. 15808959.9. (13 Pages).
Supplementary European Search Report and the European Search Opinion Dated Feb. 6, 2018 From the European Patent Office Re. Application No. 15810541.1. (11 Pages).
Translaton Dated Mar. 22, 2021 of Decision of Rejection Dated Feb. 2, 2021 From the National Intellectual Property Administration of the People's Republic of China Re. Application No. 201580043754.8. (10 Pages).
Barbucci et al. "Micro and Nano-Structured Surfaces", Journal of Materials Science: Materials in Medicine, 14(8): 721-725, Aug. 2003.
Benelli "Systane® Lubricant Eye Drops in the Management of Ocular Dryness", Clinical Ophthalmology, 5: 783-790, 2011.
Berry et al. "Hyaluronan in dry Eye and Contact Lens Wearers", Lacrimal Gland, Tear Film, and Dry Eye Syndromes 2, Chap. 110: 785-790, 1998.
Brochu "Psycho-Chemical Characterization of Layers of Intact liposomes for Drug Release Applications", University of Sherbrooke, Quebec, Canada, Thesis Submitted to the Fulfillment of the Degree of Philosophiae Doctor (Ph.D.), 113 P., Feb. 2008.
Brodie et al. "Biomechanical Properties of Achilles Tendon Repair Augmented With a Bioadhesive-Coated Scaffold", Biomedical Materials, 6(1): 015014-1-015014-16, Feb. 2011.

(56) References Cited

OTHER PUBLICATIONS

Chen et al. "Protein Repellant Silicone Surfaces by Covalent Immobilization of Poly(Ethylene Oxide)", Biomaterials, 26: 2391-2399, 2005.
Craig et al. "Effect of a Liposomal Spray on the Pre-Ocular Tear Film", Contact Lens & Anterior Eye 33(2): 83-87, XP026963833. Apr. 2010. p. 84, Left-hand Col., Line 4 -11.
Craig et al. "Importance of the Lipid Layer in Human Tear Film Stability and Evaporation", Optometry and Vision Science, 74(1): 8-13, Jan. 1997.
Das et al. "Synergistic Interactions between Grafted Hyaluronic Acid and Lubricin Provide Enhanced Wear Protection and Lubrication", Biomacromolecules, 14: 1669-1677, 2013.
Davitt et al. "Efficacy in Patients With Dry Eye After Treatment With a New Lubricant Eye Drop Formulation", Journal of Ocular Pharmacology and Therapeutics, 26(4): 347-353, 2010.
Del Castillo et al. "New Formulation Based on Liposomes and Hyaluronic Acid for Dry Eye Treatment", ARVO Annual Meeting Abstract: 1-2, XP055444902. May 2007 Retrieved from the Internet.
Desrochers et al. "Microscale Surface Friction of Articular Cartilage in Early Osteoarthritis", Journal of the Mechanical Behavior of Biomedical materials, 25: 11-22, 2013.
Ditizio et al. "A Liposomal Hydrogel for the Prevention of Bacterial Adhesion to Catheters", Biomaterials, 19: 1877-1884, 1998.
Doughty "Re-Wetting, Comfort, Lubricant and Moisturising Solutions for the Contact Lens Wearer", Contact Lens and Anterior Eye, 22(4): 116-126, 1999.
Fakes et al. "Surface Modification of a Contact Lens Co-Polymer by Plasma-Discharge Treatments", Surface and Interface Analysis, 10: 416-423, 1987.
Gaisinskaya et al. "Hydration Lubrication: Exploring a New Paradigm", Daraday Discussions, 156: 217-233, 2012.
Goddard et al. "Polymer Surface Modification for the Attachment of Bioactive Compounds", Progress in Polymer Science 32(7): 698-725, Jul. 1, 2007.
Goldberg et al. "Boundary Lubricants With Exceptionally Low Friction Coefficients Based on 2D Close-Packed Phosphatidylcholine Liposomes", Advanced Materials, 23: 3517-3521, 2011.
Goldberg et al. "Interactions Between Adsorbed Hydrogenated Soy Phsophatidylcholine (HSPC) Vesicles at Physiologically High Pressures and Salt Concentrations", Biophysical Journal, 100: 2403-2411, May 2011.
Goldberg et al. "Liposomes as Lubricants: Beyond Drug Delivery", Chemistry and Physics of Lipids, CPL, 165: 374-381, 2012.
Gulsen et al. "Dispersion of DMPC Liposomes in Contact Lenses for Ophthalmic Drug Delivery", Current Eye Research, 30: 1071-1080, 2005.
Itoi et al. "Effect of Sodium Hyaluronate Ophthalmic Solution on Peripheral Staining of Rigid Contact Lens Wearers", The CLAO Journal (Contact Lens Association of Opthalmologists), 21(4): 261-264, Oct. 1995.
Kang et al. "A New Vaginal Delivery System of Amphotericin B: A Dispersion of Cationic Liposomes in A Thermosensitive Gel", Journal of Drug Targeting, 18(8): 637-644, 2010.
Kawano et al. "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis", Arthritis & Rheumatism, 48(7): 1923-1929, Jul. 2003.
Khaireddin "Trockenes Auge bei Kontaklinsentraeger", Der Ophthalmologe 110(6): 511-515, XP055444189, Jun. 2013.
Kito et al. "Biocompatible Coatings for Luminal and Outer Surfaces of Small-Caliber Artificial Grafts", Journal of Biomedical Materials Research, 30(3): 321-330, Mar. 1996.
Klein "Hydration Lubrication", Friction, 1(1): 1-23, 2013.
Klein "Molecular Mechanisms of Synovial Joint Lubrication.", Proceedings of the Institution of Mechanical Engineers, Part J: Journal of Engineering Tribology, 220(8): 691-710, Aug. 2006.
Larsson "Biocompatible Surfaces Prepared by Immobilized Heparin or Hyaluronate", Acta Otolaryngologica, 442(Suppl.): 44-49, Jan. 1987.
Lee et al. "Shell Cross-Linked Hyaluronic Acid/Polylysine Layer-by-Layer Polyelectrolyte Microcap;sules Prepared by Removal of Reducible Hyaluronic Acid Microgel Cores", Biomacromolecules, 8(12): 3705-3711, Published Online Nov. 10, 2007.
Lee et al. "Single-Molecule Mechanics of Mussel Adhesion", Proc. Natl. Acad. Sci. USA, PNAS, 103(35): 12999-13003, Aug. 29, 2006.
Lee et al. "Thermo-Sensitive, Injectable, and Tissue Adhesive Sol-Gel Transition Hyaluronic Acid/Pluronic Composite Hydrogels Prepared from Bio-Inspired Catechol-Thiol Reaction", Soft Matter, 6: 977-983, 2010.
Ludwig et al. "The Evaluation of Viscous Ophthalmic Vehicles by Slit Lamp Fluorophotometry in Humans", International Journal of Pharmaceutics, 54: 95-102, 1989.
Mathers "Evaporation From the Ocular Surface", Experimental Eye Research, 78: 389-394, 2004.
Morra "Biochemical Modification of Titanium Surfaces: Peptides and ECM Protcins", European Cells & Materials, 12: 1-15, Jul. 24, 2006.
Morra "Engineering of Biomaterials Surfaces by Hyaluron", Biomacromolecules, 6(3): 1205-1223, Published on Web Feb. 17, 2005.
Mourtas et al. "Complex Hydrogel Systems Composed of Polymers, Liposomes, and Cyclodextrins: Implications of Composition on Rheological Properties and Aging", Langmuir, 25(15): 8480-8488, Jun. 4, 2009.
Nagarsenker et al. "Preparation and Evaluation of Liposomal Formulations of Tropicamide for Ocular Delivery", International Journal of Pharmaceutics, 190: 63-71, 1999.
Neto et al. "Nanostructured Polymeric Coatings Based on Chitosan and Dopamine-Modified Hyaluronic Acid for Biomedical Applications", Small 10(12): 2459-2469, Mar. 10, 2014.
Ngai et al. "Friction of Contact Lenses: Silicone Hydrogel Versus Conventional Hydrogel", Life Cycle Tribology, Tribology and Interface Engineering, Series 48: 371-379, 2005.
Nichols et al. "Tear Film, Conatct Lens, and Patient-Related Factors Associated With Contact Lens-Related Dry Eye", Investigative Ophthalmology & Visual Science, 47(4): 1319-1328, Apr. 2006.
Ogsten et al. "The Physiological Function of Hyaluronic Acid in Synovial Fluid; Viscous, Elastic and Lubricant Properties", Journal of Physiology, 119: 244-252, 1953.
Pasquali-Ronchetti et al. "Hyaluronan-Phospholipid Interactions", Journal of Structural Biology, 120: 1-10, 1997.
Pitt et al. "Attachment of Hyaluronan to Metallic Surfaces", Journal of Biomedical Materials Research, 68A(1): 95-106, Jan. 1, 2004.
Radin et al. "Separation of a Hyaluronate-Free Lubricating Fraction From Synovial Fluid", Nature, 288: 377-378, Oct. 24, 1970.
Rennie et al. "Friction Coefficient of Soft Contact Lenses: Measurements and Modeling", Tribology Letters, 18(4): 499-504, Apr. 2005.
Roba et al. "Friction Measurements on Contact Lenses in Their Operating Environment", Tribology Letters, 44(3): 387-397, 2011.
Seror et al. "Articular Cartilage Proteoglycans as Boundary Lubricants: Structure and Frictional Interaction of Surface-Attached Hyaluronan and Hyaluronan-Aggrecan Complexes", Biomacromolecules, 12: 3432-3443, 2011.
Seror et al. "Normal and Shear Interactions Between Hyaluronan-Aggrecan Complexes Mimicking Possible Boundary Lubricants in Articular Cartilage in Synovial Joints", Biomacromolecules, 13: 3823-3832, Oct. 17, 2012.
Simmons et al. "Conditioning of Hydrogel Lenses by a Multipurpose Solution Containing an Ocular Lubricant", CLAO Journal, 27(4): 192-194, Oct. 2001. Abstract.
Sindt et al. "Contact Lens Strategies for the Patient with Dry Eye", The Ocular Surface 5(4): 294-307, XP055158015, Oct. 2007.
Sivan et al. "Liposomes Act as Effective Biolubricants for Friction Reduction in Human Synovial Joints", Langmuir, 26(2): 1107-1116, 2010.
Sorkin et al. "Origins of Extreme Boundary Lubrication by Phosphatidylcholine Liposomes", Biomaterials, 34: 5465-5475, 2013.

(56) References Cited

OTHER PUBLICATIONS

Taglienti et al. "Investigating the Interactions of Hyaluronan Derivatives With Biomolecules. The Use of Diffusional NMR Techniques", Macromoleuclar Bioscience, 6(8): 611-622, Aug. 7, 2006.
Thai et al. "In Vitro and In Vivo Effects of a Lubricant in a Contact Lens Solution", Ophthalmic & Physiological Optics, 22(4): 319-329, Jul. 2002.
Thierry et al. "Radionuclides-Hyaluranonan-Conjugate Thromboresistant Coatings to Prevent In-Stent Restenois", Biomaterials, 25(17): 3895-3905, Aug. 2004.
Vecchio et al. "Surfactant Treatment for Osteoarthritis", Rheumatology, 38(10): 1020-1021, Oct. 1999.
Notice of Allowance Dated Sep. 13, 2023 from the Re. U.S. Appl. No. 15/319,014. (3 pages).
Official Action Dated Sep. 15, 2022 From the Re. U.S. Appl. No. 17/190,537. (28 Pages).
Requisition by the Examiner Dated May 3, 2024 From the Innovation, Science and Economic Development Canada, Canadian Intellectual Property Office Re. Application No. 3,187,647. (4 Pages).
Wang et al. "Hyaluronan and Phospholipid Association in Biolubrication", BioMacromolecules, 14(12): 4198-4206, Oct. 30, 2013. Abstract.

\* cited by examiner

SURFACE TREATMENT OF CONTACT LENS AND TREATMENT OF OCULAR DISCOMFORT BY WATER SOLUBLE POLYMERS AND LIPIDS/LIPOSOMES

RELATED APPLICATIONS

This application is a division of U.S. patent application Ser. No. 15/319,014 filed on Dec. 15, 2016, which is a National Phase of PCT Patent Application No. PCT/IL2015/050605 having International Filing Date of Jun. 15, 2015, which claims the benefit of priority under 35 USC § 119(e) of U.S. Provisional Patent Application No. 62/012,379 filed on Jun. 15, 2014. The contents of the above applications are all incorporated by reference as if fully set forth herein in their entirety.

FIELD AND BACKGROUND OF THE INVENTION

The present invention, in some embodiments thereof, relates to material science and, more particularly, but not exclusively, to solutions, articles, and/or kits, and uses thereof in surface treatment of contact lens and/or in the treatment of ocular discomfort.

Soft contact lenses are typically made of hydrogels having varying water content (e.g., from 30% to 70% wt. water). Contact lenses are widely used world-wide; globally there are over 100 million users, and the annual market value is estimated to be 7.6 billion USD. However, despite the use of hydrogels which are compatible with the eye, many users report extensive eye irritation which prevents them using such lenses for extended periods, or at all.

Many contact lens users report ocular discomfort that is attributed to dryness, e.g., dry eye symptoms. It has been assumed that ocular comfort is related, among other factors, to friction at the eye/lens interfaces—the interaction of the anterior surface of the contact lens with the under surface of the eyelid, and its posterior interface with the cornea—and several studies have accordingly been conducted in an attempt to better understand parameters that affect the sliding friction forces of contact lenses [Rennie et al., *Tribology Letters* 2005, 18:499-504; Roba et al., *Tribology Letters* 2011, 44:387-397; Ngai et al., *Tribology and Interface Engineering Series*, M. P. G. Dawson and A. A. Lubrecht, Editors. 2005, Elsevier. p. 371-379].

A review by Doughty [*Contact Lens and Anterior Eye* 1999, 22:116-126] describes various re-wetting, conform, lubricant and moisturizing solutions and their potential impact on contact lens wearers. Many of the solutions described therein include polymers such as hydroxypropylmethylcellulose (HPMC; also known as hypromellose), hydroxyethylcellulose, carboxymethylcellulose, polyethylene glycol, poloxamer, polyvinylpyrrolidone (also known as povidone) and hyaluronic acid (HA).

Simmons et al. [*CLAO J.* 2001, 27:192-194] and Thai et al. [*Ophthal. Physiol. Opt.* 2002, 22:319-329] describe that the addition of the ocular lubricant HPMC to a multipurpose contact lens solution affect physical properties of the hydrogel lens surface and tear film production, and thereby improves wetting and ocular comfort. It has been reported therein that the multipurpose solution with HPMC produced a thick and long-lasting layer of fluid on hydrogel lenses and other plastics, and that HPMC was found to adsorb to and release gradually from contact lenses.

Hyaluronic acid (HA)—in the form of a 0.1% sodium hyaluronate solution—is used as a contact lens lubricant in VisMed® Eye Drops [Doughty, *Contact Lens and Anterior Eye* 1999, 22:116-126]. HA-containing eye drops have been reported to be effective for reducing peripheral corneal staining of rigid contact lens wearers [Itoi et al., *CLAO J.* 1995, 21:261-264].

Davitt et al. [*Journal of Ocular Pharmacology and Therapeutics* 2010, 26:347-353] and Benelli [*Clinical Ophthalmology* 2011, 5:783-790] describe that management of dry eye was achieved by a formulation of polyethylene glycol 400/propylene glycol-based lubricant eye drops containing hydroxypropyl guar as a gelling agent.

Surface modification of contact lenses has also been studied as a means of reducing ocular discomfort.

Fakes et al., [*Surface and Interface Analysis* 1987, 10:416-423] have used plasma charge treatment for surface modification of alkyl acrylate/poly-siloxane co-polymer, in order to enhance surface hydrophilicity, and hence wettability of the contact lens material.

Chen et al. [*Biomaterials* 2005, 26:2391-2399] describe surface modification of polydimethylsiloxane (a material used in contact lenses) by covalent immobilization of poly (ethylene oxide), for the purpose of reducing protein adsorption.

International Patent Application publication WO 2014/071132 describes a contact lens coupled at its surface to a hyaluronic acid-binding peptide, for providing hyaluronic acid to the ocular environment by pretreating the lens with hyaluronic acid and replenishing hyaluronic acid from endogenous or exogenous sources as it is washed away or degraded.

Liposomes are vesicles whose membranes in most cases are based on phospholipid bilayers. They are generally biocompatible and, when modified with other molecules, are widely used in clinical applications, primarily as drug delivery vehicles, as well as in gene therapy and for diagnostic imaging.

Studies on surface lubrication by liposomes are described in, for example, International Patent Application Publications WO 2008/038292 and WO 2011/158237, Gaisinskaya et al. [*Faraday Discuss.* 2012, 156:217-233], Goldberg et al. [*Advanced Materials* 2011, 23:3517-3521], Goldberg et al. [*Chemistry and Physics of Lipids* 2012, 165:374-381] and Goldberg et al. [*Biophys. J.* 2011, 100:2403-2411].

The mechanism of hydration lubrication, whereby hydration layers held by surrounding charges provide effective boundary lubrication even at high pressures, is reviewed by Klein [*Friction* 2013, 1:1-23].

Gulsen et al. [*Current Eye Research* 2005, 30:1071-1080] teach contact lens compositions with drug delivery capabilities, and specifically teach dispersing exceptionally small dimyristoylphosphatidylcholine (DMPC) SUV liposomes (less than 50 nm or 80 nm in diameter) in a poly-2-hydroxyethyl methacrylate (p-HEMA) hydrogel, a common contact lens material.

Nagarsenker et al. [*International Journal of Pharmaceutics* 1999, 190:63-71] describe a use of neutral liposomes dispersed in polycarbophil gel and positively charged liposomes as an ophthalmic drug delivery system.

Additional background art includes U.S. Patent Application Publication Nos. 20040171740, 20060270781, 20100098749 and 20110293699; U.S. Pat. Nos. 7,638,137 and 8,273,366; Di Tizio et al. [*Biomaterials*, 1998, 19, p. 1877-1884]; Ludwig & van Ooteghem [*J. Pharm. Belg.* 1989, 44:391-397]; Mourtas et al. [*Langmuir* 2009, 25:8480-8488]; Kang et al. [*Journal of Drug Targeting* 2010, 18:637-644]; Pasquali-Ronchetti [*Journal of Structural Biology* 1997, 120:1-10]; Sorkin et al. [*Biomaterials*

2103, 34:5465-5475]; Berry et al. [*Hyaluronan in dry eye and contact lens wearers*. In: *Lacrimal Gland, Tear Film, and Dry Eye Syndromes* 2, D. A. Sullivan, D. A. Dartt and M. A. Meneray, Editors. 1998, Plenum Press, NY, pp. 785-790]; and Brochu, Ph.D. Thesis in the Université de Sherbrooke, Canada, 2008, Id.: 50177338.

SUMMARY OF THE INVENTION

According to an aspect of some embodiments of the present invention there is provided a solution comprising at least one water-soluble polymer, liposomes, and an aqueous carrier, the solution being for use in rinsing, and/or immersing therein, a contact lens.

According to an aspect of some embodiments of the present invention there is provided a solution comprising at least one water-soluble polymer, liposomes, and an aqueous carrier, the solution being for use in the treatment of ocular discomfort.

According to some of any of the embodiments described herein, the ocular discomfort is associated with a contact lens.

According to some of any of the embodiments described herein, the at least one water-soluble polymer comprises a non-ionic polymer.

According to some of any of the embodiments described herein, the non-ionic polymer is selected from the group consisting of a polyvinylpyrrolidone and a polyethylene glycol.

According to some of any of the embodiments described herein, the at least one water-soluble polymer comprises an ionic polymer.

According to some of any of the embodiments described herein, the ionic polymer has from 1 to 6 charged groups per 1 kDa.

According to some of any of the embodiments described herein, the ionic polymer is an anionic polymer.

According to some of any of the embodiments described herein, the anionic polymer is hyaluronic acid.

According to some of any of the embodiments described herein, the liposomes are characterized by a surface charge having a sign opposite a sign of a net charge of the ionic polymer.

According to some of any of the embodiments described herein, the at least one water-soluble polymer comprises a biopolymer.

According to some of any of the embodiments described herein, the biopolymer is selected from the group consisting of a mucin, a lubricin and a polysaccharide.

According to some of any of the embodiments described herein, a molar percentage of phosphatidylcholine in the liposomes is at least 50%.

According to some of any of the embodiments described herein, a concentration of phospholipids of the liposomes in the solution is in a range of from 0.5 mM to 500 mM.

According to some of any of the embodiments described herein, the liposomes are selected from the group consisting of small unilamellar vesicles, large unilamellar vesicles and multilamellar vesicles.

According to some of any of the embodiments described herein, the liposomes comprise multilamellar vesicles.

According to some of any of the embodiments described herein, the liposomes comprise small unilamellar vesicles.

According to some of any of the embodiments described herein, a viscosity of the solution is no more than 1000 cP.

According to some of any of the embodiments described herein, the carrier is an ophthalmically acceptable carrier.

According to an aspect of some embodiments of the present invention there is provided an article-of-manufacturing comprising the solution as described herein in any one of the embodiments thereof and any combination of these embodiments, packaged in a container, the container being configured for dispensing the solution.

According to some of any of the embodiments described herein, the container is configured for dispensing a predetermined volume of the solution.

According to an aspect of some embodiments of the present invention there is provided a kit comprising at least one contact lens and the solution as described herein in any one of the embodiments thereof and any combination of these embodiments, According to some of any of the embodiments described herein, the at least one contact lens and the solution are packaged separately.

According to some of any of the embodiments described herein, the solution is separately packaged in a container configured for dispensing the solution.

According to some of any of the embodiments described herein, the contact lens is immersed in a solution selected from the solution of the present invention and an aqueous solution other than the solution of the present invention.

According to some of any of the embodiments described herein, the contact lens is immersed in the solution.

According to an aspect of some embodiments of the present invention there is provided a method of treating ocular discomfort in a subject in need thereof, the method comprising ophthalmically administering to the subject an effective amount of the solution as described herein in any one of the embodiments thereof and any combination of these embodiment.

According to some of any of the embodiments described herein, the ocular discomfort is associated with a contact lens.

According to some of any of the embodiments described herein, the contact lens comprises a hydrogel surface.

According to some of any of the embodiments described herein, the hydrogel comprises a polymer selected from the group consisting of poly(2-hydroxyethyl methacrylate) and a silicone.

According to some of any of the embodiments described herein, the hydrogel comprises a silicone.

According to some of any of the embodiments described herein, the hydrogel comprises a polymer having no more than one negatively charged group per 2 kDa.

According to some of any of the embodiments described herein, the contact lens comprises a surface which is positively charged or neutrally charged.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to material science and, more particularly, but not exclusively, to solutions, articles, and/or kits, and uses thereof in surface treatment of contact lens and/or in the treatment of ocular discomfort.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for an improved methodology for treating ocular discomfort and/or preventing ocular discomfort frequently associated with using contact lens, the present inventors have studied the effect of a solution containing liposomes, particularly phosphatidylcholine (PC)-containing liposomes, which are known to be biocompatible, in combination with various water-soluble polymers, while using different types of commercially available contact lens, under ocular conditions, and have surprisingly uncovered that this combination considerably exceeds the lubrication effect observed in the presence of liposomes alone or the water-soluble polymers alone, resulting in a synergistic effect in reducing the friction coefficient of the tested contact lens. The lubrication effect is mediated by boundary lubrication, that is, it does not require the presence of the solution between the contact lens and ocular surface. Rather, contact with the solution results in a treated contact lens surface, wherein the surface per se is characterized by enhanced lubricity.

Figure 1A:
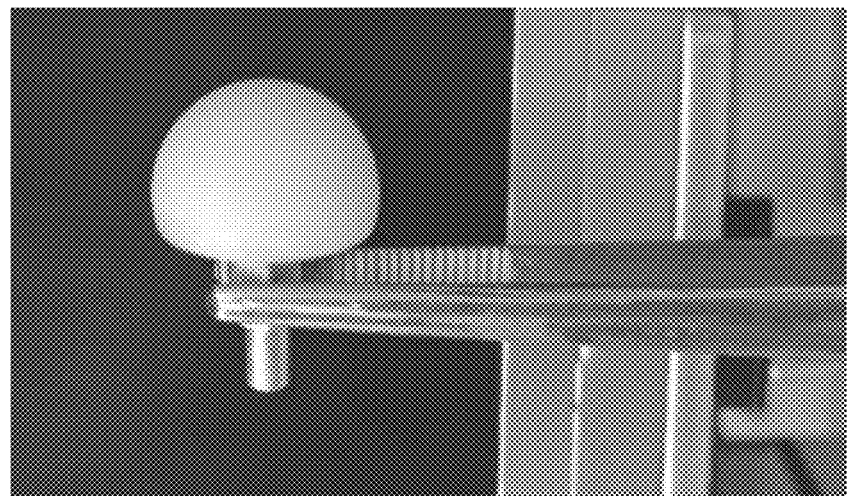
FIGS. 1A-1B present photographs of a cornea-mimicking lens holder (FIG. 1A) and the same holder with a soft contact lens mounted in place (FIG. 1B), used in some of the experiments employing a tribometer described in the Examples section hereinunder.
Figure 1B:
Figure 2:
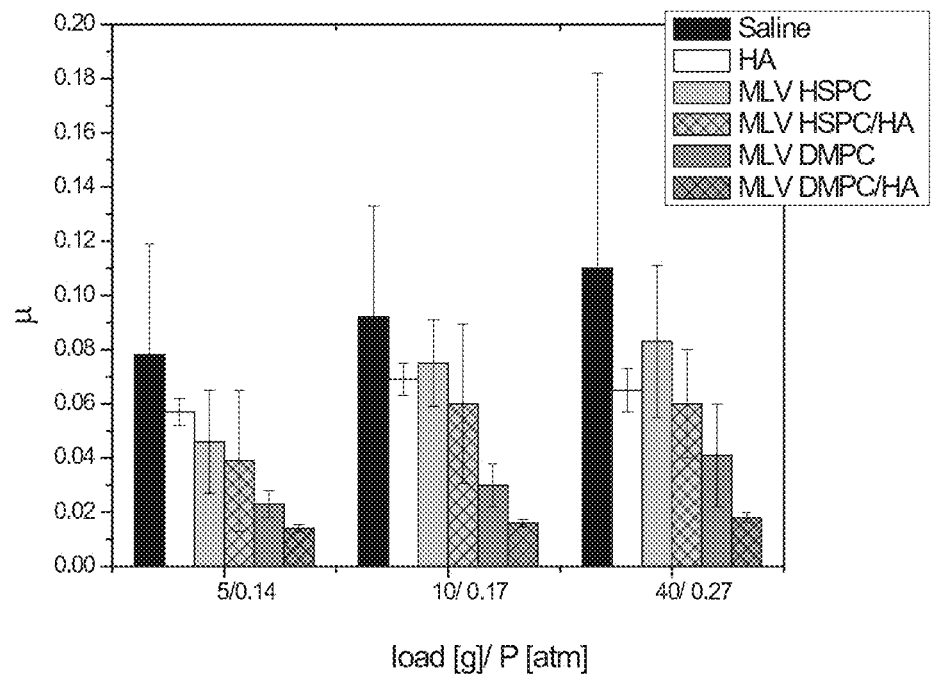
FIG. 2 presents bar graphs showing the friction coefficient of Etafilcon A contact lens upon immersion in saline, HA 1 MDa 0.2 mg/ml, MLV HSPC liposomes (45 mM), MLV HSPC liposomes+HA, MLV DMPC (45 mM), or MLV DMPC+HA, followed by rinsing with saline, as measured at a load of 5, 10 and 40 grams (corresponding respectively to mean pressures of 0.14, 0.17 and 0.27 atmospheres).
Figure 3:
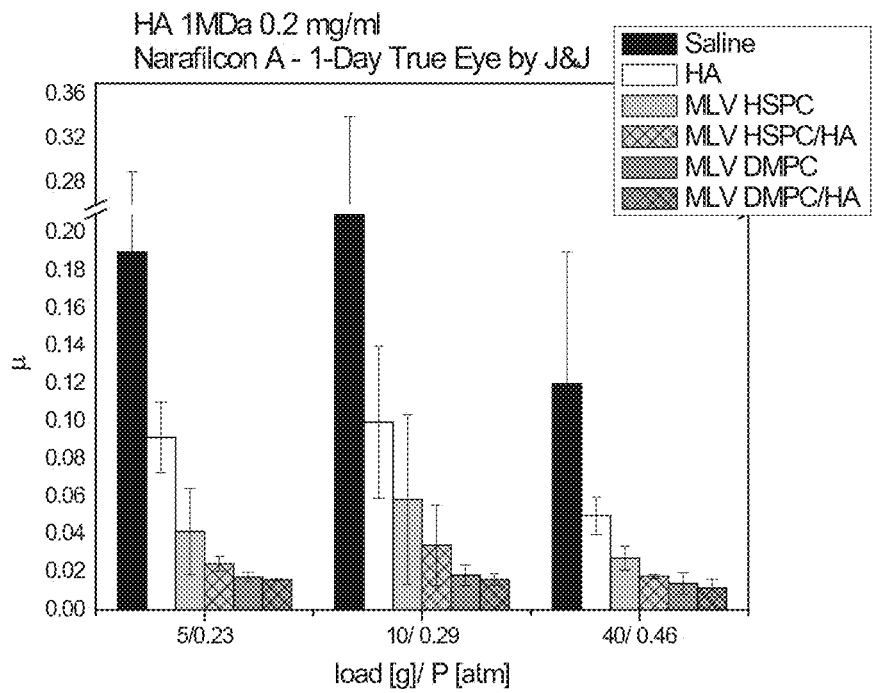
FIG. 3 presents bar graphs showing the friction coefficient of Narafilcon A contact lens upon immersion in saline, HA 1 MDa 0.2 mg/ml, MLV HSPC liposomes (45 mM), MLV HSPC liposomes+HA, MLV DMPC (45 mM), or MLV DMPC+HA, followed by rinsing with saline, as measured at a load of 5, 10 and 40 grams (corresponding respectively to mean pressures of 0.23, 0.29 and 0.46 atmosphere).
Figure 4:
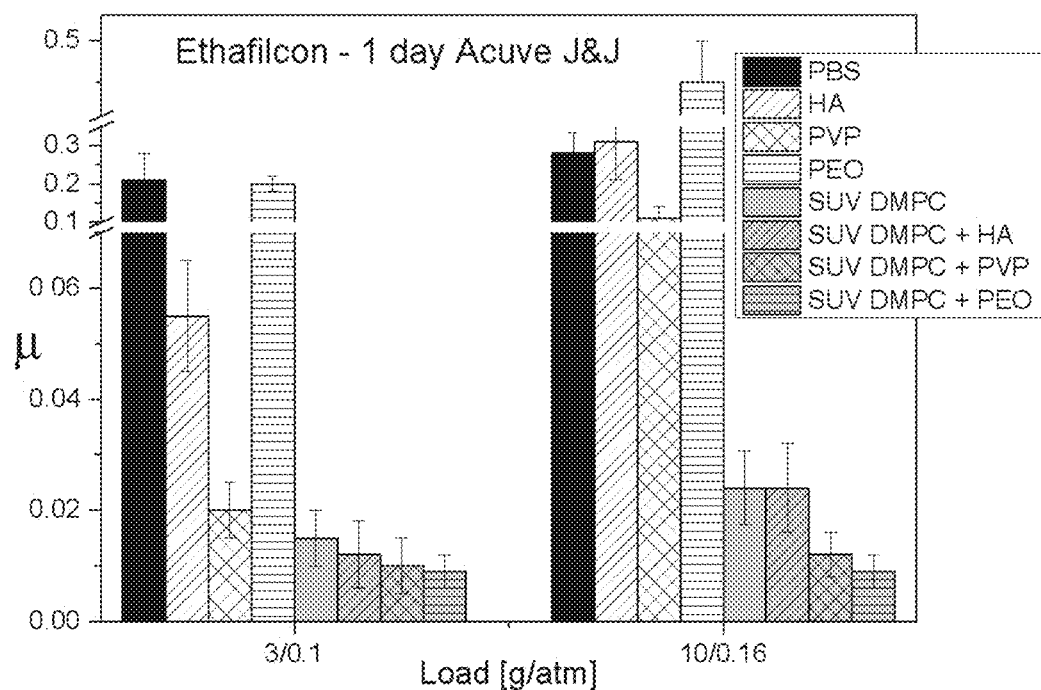
FIG. 4 presents bar graphs showing the friction coefficient of Etafilcon A contact lens upon immersion in PBS, solutions of HA, PVP or PEO (0.2 mg/ml), a solution of SUV DMPC liposomes (10 mM), or solutions of SUV DMPC liposomes with HA, PVP or PEO, followed by rinsing with PBS, as measured at a load of 3 and 10 grams (corresponding respectively to mean pressures of 0.1 and 0.16 atmospheres).

Referring now to the drawings, FIGS. 2 and 3 show that exposure of contact lenses composed of etafilcon A (FIG. 2) and narafilcon A (FIG. 3) hydrogels to liposomes (multilamellar vesicles) and hyaluronic acid (HA) enhances the lubricity of the contact lenses more effectively than does exposure to liposomes alone or HA alone (as determined using the cornea model shown in FIGS. 1A-1B). FIGS. 4-7 show that exposure of contact lenses composed of etafilcon A (FIGS. 4 and 5) and narafilcon A (FIGS. 6 and 7) hydrogels to liposomes (small unilamellar vesicles) and hyaluronic acid (HA), polyvinylpyrrolidone (PVP) or polyethylene oxide (PEO) enhances the lubricity of the contact lenses more effectively than does exposure to liposomes alone or HA, PVP or PEO, and that PVP and PEO are typically at least as effective as HA at enhancing lubricity in combination with liposomes. FIGS. 4 and 7 show that PEO exhibits particularly strong synergy with liposomes at enhancing lubricity, whereas PEO alone does not enhance lubricity at all and may even reduce lubricity.

This result surprisingly indicates that a contact lens surface contacted with a water-soluble polymer (such as HA, PVP or PEO) and liposomes is not a mosaic of a surface coated by water-soluble polymer per se and a surface coated by liposomes per se (which would result in a lubricity which is intermediate between the lubricity obtained with water-soluble polymer alone and with liposomes alone), but rather, a surface coated with water-soluble polymer and liposomes exhibits a physical characteristic which is not present in surfaces coated by water-soluble polymer alone or liposomes alone, indicating synergy between the water-soluble polymer and liposomes.

FIGS. 2-7 further show that at relatively low pressures dimyristoyl phosphatidylcholine liposomes (which are in a liquid phase) are more effective at reducing the lubricity than are hydrogenated soy phosphatidylcholine liposomes (which are in a solid phase), whereas at higher pressures, hydrogenated soy phosphatidylcholine liposomes are more effective.

Without being bound by any particular theory, it is believed that the amphiphilic lipids supplied by the liposomes provide a very low friction coefficient as a result of hydration lubrication associated with hydration of the hydrophilic moieties of the lipids. It is further believed that attachment of a water-soluble polymer to a lens surface (e.g., by adsorption) enhances lubricity by facilitating adherence of the lubricating lipids to the surface (e.g., anchoring the lipids to the surface), particularly to a lens surface which does not normally exhibit affinity to such lipids, thereby enhancing the robustness of the lubricating lipid film.

Without being bound by any particular theory, it is further believed that attachment of the water-soluble polymer to a lens surface may result in a smoother surface (e.g., by covering asperities with flexible polymer chains thereby further enhancing lubricity).

Based on the results presented herein, lubrication of a contact lens-eye interface may be effected, in accordance with various embodiments of the invention described herein.

According to an aspect of some embodiments of the invention, there is provided a formulation comprising at least one water-soluble polymer (as defined herein in any one of the respective embodiments), liposomes (as defined herein in any one of the respective embodiments), and an aqueous carrier, the solution being for use in rinsing and/or immersing therein a contact lens.

According to an aspect of some embodiments of the invention, there is provided a formulation comprising at least one water-soluble polymer (as defined herein in any one of the respective embodiments), liposomes (as defined herein in any one of the respective embodiments), and an aqueous carrier, the solution being for use in treatment of ocular discomfort.

The formulation, according to any of the aspects described herein, may optionally comprise at least one water-soluble polymer, liposomes and carrier according to any one of the embodiments described herein relating to water-soluble polymer(s) (e.g., in the section herein relating to water-soluble polymers), liposomes and lipids (e.g., in the section herein relating to liposomes and lipids), aqueous carrier and/or any combination thereof.

In some of any of the embodiments described herein, the formulation is a liquid formulation, and is also referred to herein interchangeably as "solution". It is to be noted that herein throughout, the term "solution" encompasses any liquid formulation in which the ingredients, namely, at least the water-soluble polymer and the liposomes/lipids are included within a liquid carrier, whereby each of the ingredients can be dissolved or dispersed within the carrier. The term "solution" as used herein therefore encompasses also "dispersion". The term "liquid formulation" as used herein encompasses both a solution and a dispersion.

As used herein, the term "rinsing" generally refers to brief contact (e.g., for several seconds) with a liquid (e.g., the solution described herein), whereas the term "immersing" generally refers to longer periods of contact with a liquid (e.g., the solution described herein). However, both terms refer to contact with a liquid, and are typically used herein together to encompass all forms of contact with a liquid, for example, in embodiments wherein the difference between rinsing and immersing is of no particular significance.

Without being bound by any particular theory, it is believed that rinsing and/or immersing a contact lens in a solution described herein can reduce a friction coefficient of a contact lens surface (e.g., the surface intended to be in contact with the eye and/or the surface intended to face the eyelid), thereby reducing discomfort and/or irritation associated with the contact lens in many users.

Without being bound by any particular theory, it is further believed that the solutions described herein are particularly suitable for contact with physiological surfaces such as the eye and surfaces (e.g., contact lens surfaces) which come into contact with physiological surfaces, because the liposomes and water-soluble polymer(s) may readily be selected so as to be biocompatible, optionally even be selected as substances naturally occurring in the body, and because hydration lubrication mechanism (e.g., as described herein in any one of the respective embodiments) is fully compatible with aqueous environments such as physiological environments, as opposed, for example, to lubrication via non-aqueous liquid lubricants (e.g., oils).

In some embodiments of any one of the embodiments described herein relating to ocular discomfort, the ocular discomfort is associated with a contact lens. Association of a contact lens with ocular discomfort may be based on an observation of a contact lens wearer, for example, that discomfort occurs when contact lens are being worn, and/or based on a diagnosis by a physician (e.g., ophthalmologist), for example, that an ocular discomfort (e.g., chronic discomfort) is caused by a contact lens.

In some embodiments according to any of the aspects described herein relating to a contact lens surface, the liposomes are selected such that the lipids on a contact lens surface are in a liquid phase when the contact lens is worn.

Without being bound by any particular theory, it is believed that lipids in a liquid phase are more effective than lipids in a solid phase at reducing a friction coefficient of the surface, and that the superior robustness of the solid phase is not particularly advantageous in the context of contact lenses, which are generally not subjected to high pressures. However, lipids in a solid phase can also be highly effective, as exemplified herein in the Examples section.

In some embodiments of any one of the embodiments described herein, the liposomes are characterized by a phase transition melting point (Tm) below 37° C. In some embodiments, the Tm is below 36° C. In some embodiments, the Tm is below 35° C. In some embodiments, the Tm is below 34° C. In some embodiments, the Tm is below 32° C. In some embodiments, the Tm is below 30° C. In some embodiments, the Tm is below 25° C. In some embodiments, the Tm is below 20° C.

According to another aspect of embodiments of the invention, there is provided a method of treating ocular discomfort in a subject in need thereof, the method comprising ophthalmically administering to the subject an effective amount of the solution comprising liposomes and water-soluble polymer(s), as described herein in any one of the respective embodiments. In some embodiments, the ocular discomfort is associated with a contact lens, as described herein in any one of the respective embodiments.

According to another aspect of embodiments of the invention, there is provided a use of the solution comprising liposomes and water-soluble polymer(s), as described herein in any one of the respective embodiments, in the manufacture of a medicament for treating ocular discomfort. In some embodiments, the ocular discomfort is associated with a contact lens, as described herein in any one of the respective embodiments.

It is expected that during the life of a patent maturing from this application many relevant contact lens, hydrogels for forming contact lens, and liposomes will be developed and the scope of the terms "contact lens" and "liposomes" is intended to include all such new technologies a priori.

Liposomes and Lipids:

The liposomes and/or lipids according to any one of the embodiments described in this section may be used in the context of any one of the embodiments of any of the aspects of the inventions described herein.

As used herein and in the art, the term "liposome" refers to an artificially prepared vesicle comprising a bilayer composed of molecules of an amphiphilic lipid. In an aqueous medium, the bilayer is typically configured such that hydrophilic moieties of the amphiphilic lipid are exposed to the medium at both surfaces of the bilayer, whereas lipophilic moieties of the lipid are located in the internal portion of the bilayer, and therefore less exposed to the medium. Examples of liposomes which may be used in any one of the embodiments described herein include, without limitation, small unilamellar vesicles, large unilamellar vesicles and multilamellar vesicles.

In some embodiments of any one of the embodiments described herein, the liposomes comprise multilamellar vesicles. In some embodiments, the liposomes are primarily (more than 50 weight percents) multilamellar vesicles.

In some embodiments of any one of the embodiments described herein, the liposomes comprise small unilamellar vesicles. In some embodiments, the liposomes are primarily (more than 50 weight percents) small unilamellar vesicles.

In some embodiments of any one of the embodiments described herein, the liposomes comprise large unilamellar vesicles. In some embodiments, the liposomes are primarily (more than 50 weight percents) large unilamellar vesicles.

As used herein, the term "unilamellar" refers to liposomes characterized by a single lipid bilayer, whereas the term "multilamellar" refers to liposomes characterized by a multiple lipid bilayers, for example, concentric bilayers.

As used herein, the phrase "small unilamellar vesicle" refers to unilamellar liposomes of less than 100 nm in diameter, whereas the phrase "large unilamellar vesicle" refers to unilamellar liposomes at least 100 nm in diameter.

As used herein, the term "amphiphilic lipid" refers to compounds comprising at least one hydrophilic moiety and at least one lipophilic moiety. Examples of amphiphilic lipids include, without limitation, fatty acids (e.g., at least 6 carbon atoms in length) and derivatives thereof such as phospholipids and glycolipids; sterols (e.g., cholesterol) and steroid acids.

Herein, the term "phospholipid" refers to a compound comprising a substituted or non-substituted phosphate group and at least one alkyl chain (optionally at least two alkyl chains) which is optionally at least 5 carbon atoms in length, optionally at least 7 atoms in length and optionally at least 9 atoms in length. The at least one alkyl chain is optionally a part of an acyl group (e.g., a fatty acid residue) or an alkyl group per se (e.g., a fatty alcohol residue). In some embodiments, the phosphate group and on e or two (optionally two) alkyl chains (e.g., acyl or alkyl) are attached to a glycerol moiety via the oxygen atoms of glycerol.

In some embodiments of any one of the embodiments described herein, the amphiphilic lipids coating a surface and/or substrate described herein (e.g., a contact lens surface, a physiological surface, and/or a surface whose friction coefficient is being reduced, according to any one of the respective embodiments described herein) are in the form of intact liposomes, optionally essentially the same liposomes (e.g., essentially the same mass and molecular composition) contacted with the water-soluble polymer(s).

In some embodiments of any one of the embodiments described herein, at least a portion of the amphiphilic lipids (optionally substantially all of the lipids) coating the surface are in a form substantially different than the liposomes from which the lipids are derived. In some embodiments, during the coating for the surface, liposomes are converted to open layers (e.g., lipid bilayers and/or lipid monolayers), as opposed to the closed vesicular structure of the liposomes. Accordingly, any reference herein to coating a surface with liposomes should not be interpreted as meaning that an obtained coated surface comprises liposomes, only that liposomes are utilized by the methodology (e.g., as an ingredient).

As used herein, the term "phospholipid" encompasses lipids having a (phosphorylated) glycerol backbone (e.g., monoacylglyceride and/or diacylglyceride phospholipids), referred to as glycerophospholipids; and lipids having a (phosphorylated) sphingosine backbone, referred to as phosphosphingolipids (e.g., sphingomyelins).

As used herein, the term "glycolipid" encompasses lipids having a (glycosylated) glycerol backbone (e.g., monoacylglyceride and/or diacylglyceride glycolipids), referred to as glyceroglycolipids; and lipids having a (glycosylated) sphingosine backbone, referred to as glycosphingolipids (e.g., cerebrosides, gangliosides).

In some embodiments of any one of the embodiments described herein, the hydrophilic moiety is an ionic moiety.

Herein, the phrase "ionic moiety" refers to a moiety which comprises at least one charged group (as defined herein), and includes anionic moieties (which have a net negative charge), cationic moieties (which have a net positive charge) and zwitterionic moieties (which have an equal number of positive and negative charges, and thus, no net charge).

Without being bound by any particular theory, it is believed that ionic moieties are particularly effective at binding to water molecules, which renders lipid molecules comprising such moieties particularly effective at promoting hydration lubrication, in which the bound water molecules provide lubrication even at high pressures.

In some embodiments of any one of the embodiments described herein, the amphiphilic lipid comprises at least one phospholipid. Phospholipids are typically characterized by the presence of an ionic moiety which includes a negative charge associated with an oxygen atom in a phosphate moiety (P—O$^-$), although additional charges may be present.

In some embodiments of any one of the embodiments described herein, the phospholipid is a glycerophospholipid. In some embodiments, the glycerophospholipid is a diacylglyceride, comprising two fatty acyl groups and one phosphate group attached to a glycerol backbone.

In some embodiments of any one of the embodiments described herein, a concentration of phospholipids in liposomes in a solution described herein is in a range of from 0.5 mM to 500 mM. In some embodiments, the concentration is in a range of from 1.5 mM to 150 mM. In some embodiments, the concentration is in a range of from 5 mM to 50 mM.

In some embodiments of any one of the embodiments described herein, a concentration of phospholipids in liposomes in a solution described herein is in a range of from 0.5 mM to 50 mM. In some embodiments, the concentration is in a range of from 1.5 mM to 50 mM.

In some embodiments of any one of the embodiments described herein, a concentration of phospholipids in liposomes in a solution described herein is in a range of from 5 mM to 500 mM. In some embodiments, the concentration is in a range of from 5 mM to 150 mM.

In some embodiments of any one of the embodiments described herein, the amphiphilic lipid comprises at least one negatively charged atom and at least one positively charged atom. In some embodiments, the amphiphilic lipid is zwitterionic, that is, the one or more negative charges in the molecule are balanced out by an equal number of positive charge(s) in the molecule. In some embodiments, the amphiphilic lipid comprises exactly one negative charge and one positive charge.

In some embodiments of any one of the embodiments described herein, the amphiphilic lipid comprises at least one phospholipid which comprises a phosphoethanolamine group or N-alkyl derivative thereof.

The phrase "phosphoethanolamine group or N-alkyl derivative thereof" refers to a —O—P(=O)(—O⁻)—OCH$_2$CH$_2$NR'R"R'"⁺ group (or a salt thereof), wherein R', R" and R'" are each independently hydrogen or alkyl, preferably C$_{1-4}$ alkyl. In some embodiments of any one of the embodiments described herein, the alkyl group(s) attached to the nitrogen atom are each independently methyl or ethyl. In some embodiments, the alkyl(s) is methyl. The term "phosphoethanolamine" refers to a group wherein R', R" and R'" are each hydrogen. The term "phosphocholine" refers to a group wherein R', R" and R'" are each methyl.

Without being bound by any particular theory, it is believed that the distance between the positive and negative charges in a phosphoethanolamine group or N-alkyl derivative thereof is particularly suitable for binding water molecules and/or promoting hydration lubrication.

In some embodiments of any one of the embodiments described herein, a molar percentage of the phospholipid described herein (e.g., in liposomes described herein) which comprises a phosphoethanolamine group or N-alkyl derivative thereof is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the phospholipid consists essentially of at least one phospholipid comprising a phosphoethanolamine group or N-alkyl derivative thereof.

In some embodiments of any one of the embodiments described herein, a molar percentage of the amphiphilic lipid described herein (e.g., in liposomes described herein) which consists of at least one phospholipid which comprises a phosphoethanolamine group or N-alkyl derivative thereof is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the amphiphilic lipid consists essentially of at least one phospholipid which comprises a phosphoethanolamine group or N-alkyl derivative thereof.

In some embodiments of any one of the embodiments described herein, the at least one phospholipid comprises at least one phosphatidylcholine.

Herein and in the art, the term "phosphatidylcholine" refers to a glycerophospholipid comprising a phosphocholine group and two fatty acyl groups attached to a glycerol backbone (i.e., a diacylglyceride).

In some embodiments of any one of the embodiments described herein, the phospholipid described herein (e.g., in liposomes described herein) is characterized by a molar percentage of phosphatidylcholine (the at least one phosphatidylcholine described herein) which is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the phospholipid consists essentially of at least one phosphatidylcholine.

In some embodiments of any one of the embodiments described herein, the amphiphilic lipid described herein (e.g., in liposomes described herein) is characterized by a molar percentage of phosphatidylcholine (the at least one phosphatidylcholine described herein) which is at least 20%. In some embodiments, the molar percentage is at least 40%. In some embodiments, the molar percentage is at least 50%. In some embodiments, the molar percentage is at least 60%. In some embodiments, the molar percentage is at least 70%. In some embodiments, the molar percentage is at least 80%. In some embodiments, the molar percentage is at least 90%. In some embodiments, the amphiphilic lipid consists essentially of at least one phosphatidylcholine.

The fatty acyl groups in a lipid described herein may comprise saturated fatty acyl groups, monounsaturated fatty acyl groups (having a single unsaturated bond) and/or polyunsaturated fatty acyl groups (having two or more unsaturated bonds). In some embodiments, the unsaturated bonds are cis double bonds.

Examples of suitable saturated fatty acyl groups include, without limitation, lauroyl, myristoyl, palmitoyl and stearoyl.

Examples of suitable monounsaturated fatty acyl groups include, without limitation, oleoyl, palmitoleoyl, eicosenoyl, erucoyl, nervonoyl and vaccenoyl.

Examples of suitable polyunsaturated fatty acyl groups include, without limitation, linoleoyl, α-linolenoyl, γ-linolenoyl, dihomo-γ-linolenoyl, stearidonoyl, eicosatetraenoyl, eicosapentaenoyl, docosapentaenoyl, docosahexaenoyl, arachidonoyl and adrenoyl.

In some embodiments of any one of the embodiments described herein, the fatty acyl groups are selected from the group consisting of saturated and monounsaturated fatty acyl groups. In some embodiments, the fatty acyl groups are saturated fatty acyl groups.

Without being bound by any particular theory, it is believed that saturated and monounsaturated fatty acyl groups, particularly saturated fatty acyl groups, are relatively resistant to chemical reaction such as oxidation, and therefore provide a more resilient system.

In some embodiments of any one of the embodiments described herein, at least 50% of the fatty acyl groups are the same species of fatty acyl group (e.g., myristoyl, palmitoyl). In some embodiments, at least 75% of the fatty acyl groups are the same species of fatty acyl group. In some embodiments, at least 90% of the fatty acyl groups are the same species of fatty acyl group.

Exemplary phospholipids comprising a single species of fatty acyl group include 1,2-dimyristoyl-sn-glycero-3-phosphocholine and 1,2-dipalmitoyl-sn-glycero-3 phosphocholine.

It is to be appreciated that phase transitions, e.g., melting points (Tm), of the lipid bilayers and liposomes described herein may be determined by the skilled person by selecting suitable fatty acyl groups for inclusion in the lipids, for example, by selecting relatively short and/or unsaturated fatty acyl groups (e.g., myristoyl) to obtain a relatively low melting point; and/or by selecting relatively long and/or saturated fatty acyl groups (e.g., palmitoyl and/or stearoyl) to obtain a relatively high melting point.

In some embodiments of any one of the embodiments described herein, the liposomes described herein are characterized by a phase transition melting point above an expected ambient temperature of a surface to which the liposomes are applied (e.g., as described herein in any one of the respective embodiments), such that a surface coated by lipids at the expected ambient temperature will be coated predominantly by lipids in a solid phase. For example, in some embodiments, liposomes characterized by a melting point above a physiological temperature (e.g., about 37° C.) are used to coat a physiological surface with lipids (e.g., as described herein in any one of the respective embodiments).

Without being bound by any particular theory, it is believed that lipid coatings in a solid phase are more resilient than lipid coatings in a liquid phase, and are therefore particularly suitable for providing lubrication to surfaces for a prolonged period of time and/or surfaces (e.g., articular surfaces of joints) subject to high pressures (e.g., 10 atmospheres or more).

In some embodiments of any one of the embodiments described herein, the liposomes described herein are characterized by a phase transition melting point below an expected ambient temperature of a surface to which the liposomes are applied (e.g., as described herein in any one of the respective embodiments), such that a surface coated by lipids at the expected ambient temperature will be coated predominantly by lipids in a liquid phase. For example, in some embodiments, liposomes characterized by a melting point below a physiological temperature (e.g., about 36° C.) are used to coat a physiological surface with lipids (e.g., as described herein in any one of the respective embodiments).

Without being bound by any particular theory, it is believed that lipid coatings in a liquid phase provide the most effective lubrication at low pressures (e.g., below 10 atmospheres) where a particularly prolonged period of lifetime is not crucial, and are therefore particularly suitable for providing lubrication to surfaces (e.g., contact lens surfaces) which are generally not subjected to such high pressures and which may be readily replaced (e.g., as in disposable contact lenses) and/or re-coated with a lipid.

In some embodiments of any one of the embodiments described herein, the liposomes described herein are characterized by a surface charge, which may be a positive surface charge or a negative surface charge.

As used herein, the phrase "surface charge" refers to an electric charge at or near a surface, such as an interface of a liposome with a solution. The phrase "surface charge" encompasses an electric charge associated with an electric potential at a surface (e.g., such that a positive electric potential at a surface is indicative of a positive surface charge, whereas a negative electric potential at a surface is indicative of a negative surface charge); as well as an electric charge which is closer to a surface than an electric charge of an opposite sign (e.g., as in a zwitterion wherein the positive charge is closer to the surface than the negative charge, or vice versa), such that an ion near the surface will interact primarily with the electric charge near the surface (due to the proximity) as opposed to the electric charge of an opposite sign. For example, phosphatidylcholine liposomes typically exhibit a positive surface charge because the positive charge of the choline group is closer to the liposome surface than the negative charge of the phosphate group.

Optionally, a surface charge of a liposome is associated with a net charge of the lipid molecules in the liposome, for example, a liposome comprising anionic lipids has a negative surface charge, and/or a liposome comprising cationic lipids has a positive surface charge.

Alternatively or additionally, a surface charge of a liposome is associated with a dipole of lipid molecules (e.g., zwitterionic lipid molecules) in the liposome, for example, a liposome comprising a zwitterionic lipid comprising a phosphocholine group may have a positive surface charge due to the positively charged ammonium groups in the phosphocholine groups being (on average) closer to the surface of the liposomes than the negatively charged phosphate groups in the phosphocholine groups.

The skilled person will be readily capable of determining a surface charge. For example, the sign of a surface charge may be determined by comparing the propensity of a surface (e.g., of a liposome) to bind to anionic vs. cationic compounds (e.g., labeling compounds). Alternatively, or in addition, surface charge can be determined by zeta potential measurements, using techniques well known in the art.

In some embodiments of any one of the embodiments described herein, the liposomes rupture upon contact with the water-soluble polymer(s) (e.g., on a surface). Liposome rupture may optionally result in a lipid bilayer in the liposomes being converted from a curved geometry (e.g., as in the relatively spherical liposomes) to a flatter geometry which complements the geometry of the surface and/or the water-soluble polymer(s) attached to the surface (e.g., thereby enhancing affinity of the lipids to the surface); and/or which results in a flatter, smoother lipid-coated surface (e.g., thereby further reducing friction).

Without being bound by any particular theory, it is believed that rupture of liposomes is induced by affinity of the surface-attached water-soluble polymer(s) to the lipids in the liposome, whereby rupture of the liposomes allows a greater area of the surface-attached water-soluble polymer(s) to come into contact with lipids, thereby increasing an amount of energetically favorable interactions between the water-soluble polymer(s) and lipid.

In some embodiments of any one of the embodiments described herein, liposomes and water-soluble polymer(s) are selected such that the selected water-soluble polymer(s) is effective at rupturing the selected liposomes.

Water-Soluble Polymer(s):

The water-soluble polymer(s) according to any one of the embodiments described in this section may be used in the context of any one of the embodiments of any of the aspects of the inventions described herein, and in combination with liposomes and/or lipids according to any one of the embodiments described herein with respect to liposomes and/or lipids.

As used herein, the phrase "water-soluble polymer" encompasses polymers having a solubility of at least 1 gram per liter in an aqueous (e.g., water) environment at pH 7 (at 25° C.).

In some embodiments of any of the embodiments described herein, the water-soluble polymer has a solubility of at least 2 grams per liter (under the abovementioned conditions). In some embodiments, the solubility is at least 5 grams per liter. In some embodiments, the solubility is at least 10 grams per liter. In some embodiments, the solubility is at least 20 grams per liter. In some embodiments, the solubility is at least 50 grams per liter. In some embodiments, the solubility is at least 100 grams per liter.

The water-soluble polymer(s) according to any pf the embodiments described herein may comprise at least one ionic polymer and/or at least one non-ionic polymer which is water-soluble as defined herein.

As used herein, the phrase "non-ionic polymer" refers to a polymer which does not have a charged group.

Examples of suitable non-ionic water-soluble polymers include, without limitation, polyvinylpyrrolidone (also referred to herein interchangeably as povidone and/or PVP)

and polyethylene oxide (also referred to herein interchangeably as PEO, PEG and/or polyethylene glycol).

As used herein, the phrase "ionic polymer" refers to polymers having at least one charged group, and encompasses polymers having a net negative charge (also referred to herein as "anionic polymers"), polymers having a net positive charge (also referred to herein as "cationic polymers"), and polymers having no net charge (also referred to herein as "zwitterionic polymers"), in an aqueous (e.g., water) environment at pH 7.

Herein throughout, the phrase "charged group" refers to any functional group (e.g., a functional group described herein) which is ionic (as defined herein), including, for example, amine, carboxylic acid, sulfate, sulfonate, phosphate and phosphonate. Thus, each electric charge in a moiety or molecule is associated with one charged group, although a single charged group (e.g., non-substituted phosphate) may be associated with more than one electric charge of the same sign (e.g., a dianion, a dication).

Herein throughout, the term "ionic" refers to the presence of an electric charge on at least one atom in a moiety and/or molecule (in at least 50% of moieties and/or molecules in a population) in an aqueous medium (e.g., water) at pH 7. The electric charge may be negative (anionic) or positive (cationic). If more than one electric charge is present, the electric charges may be negative (anionic) and/or positive (cationic), for example, both a negative and a positive charge may be present (zwitterionic).

In some embodiments of any one of the embodiments described herein relating to an ionic polymer, at least 75% of the ionic groups in the polymer have the same charge, that is, at least 75% of the ionic groups are cationic groups or are anionic groups, such that the polymer is substantially cationic or anionic, respectively. In some embodiments, at least 90% of the ionic groups in the polymer have the same charge. In some embodiments, at least 95% of the ionic groups in the polymer have the same charge. In some embodiments, at least 98% of the ionic groups in the polymer have the same charge. In some embodiments, at least 99% of the ionic groups in the polymer have the same charge.

In some embodiments of any one of the embodiments described herein, about 50% of the ionic groups in the polymer have a positive charge and about 50% of the ionic groups in the polymer have a negative charge, such that the polymer is substantially zwitterionic.

In some embodiments of any one of the embodiments described herein, the ionic polymer is characterized by a charge density of from 1 to 6 charged groups (ionic groups) per 1 kDa molecular weight of the polymer. In some embodiments, the ionic polymer has from 1.5 to 4 charged groups per 1 kDa. In some embodiments, the ionic polymer has from 2 to 3 charged groups per 1 kDa.

In some embodiments of any one of the embodiments described herein, the ionic polymer is characterized by a net charge (i.e., the difference between the number of anionic groups and the number of cationic groups) of from 1 to 6 electric charges per 1 kDa molecular weight of the polymer. In some embodiments, the ionic polymer has a net charge of from 1.5 to 4 charges per 1 kDa. In some embodiments, the ionic polymer has a net charge of from 2 to 3 charges per 1 kDa.

In some embodiments of any one of the embodiments described herein, the ionic polymer is an anionic polymer, for example, a polymer characterized by a net negative charge of from 1 to 6 electric charges per 1 kDa molecular weight of the polymer.

In some embodiments of any one of the embodiments described herein, the ionic polymer is a cationic polymer, for example, a polymer characterized by a net positive charge of from 1 to 6 electric charges per 1 kDa molecular weight of the polymer.

In some embodiments of any one of the embodiments described herein, the ionic polymer is a polysaccharide (which is an ionic polysaccharide).

As used herein throughout, the term "polysaccharide" refers to a polymer composed primarily (at least 50 weight percents) of monosaccharide units linked by glycosidic linkages.

As used herein, the term "monosaccharide" encompasses carbohydrates per se (having the formula $Cn(H_2O)n$, wherein n is at least 3, typically from 3 to 10), as well as derivatives thereof such as amino sugars, in which at least one hydroxyl group is replaced by an amine or amide group; sugar acids, in which one or two carbon atoms are oxidized to form a carboxylate group; acylated monosaccharides, in which at least one hydroxyl group and/or amine group is substituted by an acyl group (e.g., acetyl); and sulfated monosaccharides, in which at least one hydroxyl group is replaced by a sulfate group.

Examples of monosaccharides include, without limitation, hexoses (e.g., D-hexoses and/or L-hexoses) such as allose, altrose, glucose, mannose, gulose, idose, galactose, talose, psicose, fructose, sorbose and tagatose; pentoses (e.g., D-pentoses and/or L-pentoses) such as arabinose, lyxose, xylose, ribose, ribulose and xylulose; and hexose derivatives such as glucuronic acid, iduronic acid, manuronic acid, guluronic acid, glucosamine and N-alkyl derivatives thereof, galactosamine and N-alkyl derivatives thereof, N-acetylglucosamine, N-acetylgalactosamine, and monosulfated and disulfated N-acetylgalactosamine, glucuronic acid and iduronic acid.

As used herein, the phrase "glycosidic linkage" refers to a bond between a hemiacetal group of one compound (e.g., a monosaccharide monomer) and a hydroxyl group of another compound (e.g., another monosaccharide monomer).

Examples of ionic polysaccharides include, without limitation, hyaluronic acid, chondroitin sulfate, alginic acid, xanthan gum, chitosan and N-alkyl chitosan derivatives.

Hyaluronic acid is an anionic polysaccharide comprising anionic glucuronic acid monomer units along with non-ionic N-acetylglucosamine monomer units. Hyaluronic acid is an exemplary anionic polymer.

Chondroitin sulfate is an anionic polysaccharide comprising anionic sulfated (e.g., monosulfated and/or disulfated) N-acetylgalactosamine, glucuronic acid and/or iduronic acid monomer units, and anionic glucuronic acid and/or iduronic acid monomer units, along with non-ionic N-acetylgalactosamine monomer units.

Alginic acid is an anionic polysaccharide comprising anionic mannuronic acid and guluronic acid monomer units.

Xanthan gum is an anionic polysaccharide comprising anionic glucuronic acid monomer units, along with non-ionic glucose and mannose monomer units (including acetyl and/or pyruvyl derivatives thereof).

Chitosan is a cationic polysaccharide comprising cationic glucosamine monomer units, optionally along with non-ionic N-acetylglucosamine monomer units. In N-alkyl chitosan derivatives, at least a portion of the glucosamine units comprise 1, 2 or 3 alkyl groups, preferably $C_{1-4}$ alkyl, attached to the nitrogen atom. In some embodiments of any one of the embodiments described herein, the alkyl groups attached to the nitrogen atoms are each independently methyl or ethyl. In some embodiments, the alkyls are methyl. In some embodiments, the N-alkylated monomer unit is N-trimethylglucosamine.

Herein, the terms "hyaluronic acid", "chondroitin sulfate", "alginic acid", "xanthan gum", "chitosan", "N-alkyl chitosan derivatives" and any other ionic compounds named herein, encompass all salts of the named compounds along with the non-ionic forms (e.g., acid forms of the anionic polysaccharides, and the free base forms of the cationic polysaccharides).

Without being bound by any particular theory, it is believed that hyaluronic acid on a surface is particularly effective at binding to liposomes and rupturing them, thereby forming a lipid coating (e.g., lipid bilayer) with relatively high affinity to a surface, such as a contact lens surface.

It is further believed that hyaluronic acid is particularly suitable for use in the context of contact lenses, as hyaluronic acid is naturally present on the ocular surface.

In some embodiments of any one of the embodiments described herein, the polysaccharide is in a form of a salt. In some embodiments, the salt is a pharmaceutically acceptable salt (e.g., an ophthalmically acceptable salt for an ophthalmic application described herein, a salt suitable for parenteral administration for a parenteral application described herein).

In some embodiments of any one of the embodiments described herein, the polysaccharide has from 0.2 to 1 charged groups per monosaccharide residue. In some embodiments, the polysaccharide has from 0.2 to 0.9 charged groups per monosaccharide residue. In some embodiments, the polysaccharide has from 0.3 to 0.7 charged groups per monosaccharide residue. In some embodiments, the polysaccharide has from 0.4 to 0.6 charged groups per monosaccharide residue. In some embodiments, the polysaccharide has about 0.5 charged groups per monosaccharide residue.

It is to be appreciated that a monosaccharide residue may comprise more than one charged group (e.g., a sulfate group and a carboxylate group).

In some embodiments of any one of the embodiments described herein, the monosaccharide residues comprise no more than one charged group, that is, 0 or 1 charged group.

In some embodiments of any one of the embodiments described herein, the polysaccharide is characterized by a net charge (i.e., the difference between the number of anionic groups and the number of cationic groups) of from 0.2 to 1 electric charges per monosaccharide residue. In some embodiments, the net charge is from 0.2 to 0.9 electric charges per monosaccharide residue. In some embodiments, the net charge is from 0.3 to 0.7 electric charges per monosaccharide residue. In some embodiments, the net charge is from 0.4 to 0.6 electric charges per monosaccharide residue. In some embodiments, the net charge is about 0.5 electric charges per monosaccharide residue.

In some embodiments of any one of the embodiments described herein, the water-soluble polymer comprises one or more biopolymers.

Herein, the term "biopolymer" refers to a polymer naturally occurring in a living organism. Examples of biopolymers include, without limitation, polynucleotides (e.g., RNA and DNA), polypeptides, polysaccharides and conjugates thereof (e.g., glycoproteins and proteoglycans comprising polypeptide and polysaccharide moieties). It is to be appreciated that biopolymers may optionally comprise many different species of related monomeric units (e.g., about 20 different types of amino acid residues and/or various types of monosaccharide moieties) with little or no repetition of the specific species of monomeric units, yet are considered polymers because at least some of the monomeric units are related in structure (e.g., being amino acid residues or monosaccharide moieties).

In some embodiments of any one of the embodiments described herein, the biopolymer(s) comprises a polypeptide (optionally attached to one or more saccharide moieties) and/or a polysaccharide.

Examples of suitable biopolymers comprising a polypeptide include, without limitation, mucins and lubricin.

Herein, the term "lubricin" refers to a proteoglycan (also known in the art as "proteoglycan 4") of about 345 kDa. Human lubricin is encoded by the PRG4 gene. The lubricin optionally comprises a polypeptide sequence of isoform A and/or isoform B of lubricin, e.g., according to NCBI reference sequence NP_001121180.

Herein, the term "mucin" refers to a family of high molecular weight glycosylated proteins produced by many animals, and encompasses human mucins such as, for example, mucin 1 (e.g., according to NCBI reference sequence NP_001018016), mucin 2 (e.g., according to NCBI reference sequence NP_002448), mucin 3A (e.g., according to NCBI reference sequence NP_005951), mucin 3B, mucin 4 (e.g., according to NCBI reference sequence NP_004523), mucin 5AC, mucin 5B (e.g., according to NCBI reference sequence NP_002449), mucin 6 (e.g., according to NCBI reference sequence NP_005952), mucin 7 (e.g., according to NCBI reference sequence NP_001138478), mucin 8, mucin 12, mucin 13, mucin 15, mucin 16 (e.g., according to NCBI reference sequence NP_078966), mucin 17 (e.g., according to NCBI reference sequence NP_001035194), mucin 19, and mucin 20 (e.g., according to NCBI reference sequence NP_001269435).

The polysaccharide may be a non-ionic polymer (as defined herein) or an ionic polymer (as defined herein), e.g., according to any of the embodiments described herein relating to an ionic polysaccharide.

Hyaluronic acid (e.g., according to any of the respective embodiments described herein) is a non-limiting example of a suitable polysaccharide as well as a non-limiting example of a suitable anionic polymer.

In some embodiments of any one of the embodiments described herein, the water-soluble polymer(s) is selected to enhance an affinity of the liposomes to the surface of a contact lens (according to any of the respective embodiments described herein), that is, the liposome lipids have a greater affinity to the surface coated by the water-soluble polymer(s) than to the surface in the absence of the water-soluble polymer(s).

In some embodiments of any one of the embodiments described herein, the water-soluble polymer(s) comprises an ionic polymer selected such that the liposomes are characterized by a surface charge having a sign opposite a sign of a net charge of the ionic polymer.

In some embodiments of any one of the embodiments described herein, the liposomes are characterized by a negative surface charge (e.g., as described herein in any one of the respective embodiments) and the water-soluble polymer(s) comprises an ionic polymer having a net positive charge (e.g., as described herein in any one of the respective embodiments). In some embodiments, the ionic polymer is a polysaccharide having a net positive charge (e.g., a cationic polysaccharide described herein in any one of the respective embodiments).

In some embodiments of any one of the embodiments described herein, the liposomes are characterized by a positive surface charge (e.g., as described herein in any one of the respective embodiments) and the water-soluble polymer(s) comprises an ionic polymer having a net negative charge (e.g., as described herein in any one of the respective embodiments). In some embodiments, the ionic polymer is a polysaccharide having a net negative charge (e.g., an anionic polysaccharide described herein in any one of the respective embodiments). In some embodiments, the ionic polymer is hyaluronic acid (optionally hyaluronate salts, in accordance with the definition of "hyaluronic acid" used herein).

In some embodiments of any one of the embodiments described herein, the amphiphilic lipid comprises at least one phospholipid which comprises a phosphoethanolamine group or N-alkyl derivative thereof (e.g., in any one of the respective embodiments) and the water-soluble polymer(s) comprises an ionic polymer having a net negative charge (e.g., as described herein in any one of the respective embodiments). In some embodiments, the ionic polymer is a polysaccharide having a net negative charge (e.g., an anionic polysaccharide described herein). In some embodiments, the ionic polymer is hyaluronic acid.

Herein throughout, the term "at least one" means that the formulation or solution comprises one water-soluble polymer or a mixture of two or more water-soluble polymers.

In some embodiments of any of the embodiments described herein, the formulation or solution comprises one water-soluble polymer.

In some embodiments of any of the embodiments described herein, the water-soluble polymers described herein comprise at least two water-soluble polymers according to any of the respective embodiments described herein. In some embodiments, the water-soluble polymers comprise at least three water-soluble polymers according to any of the respective embodiments described herein.

In some embodiments of any of the embodiments described herein, the water-soluble polymers described herein comprise at least one biopolymer (according to any of the respective embodiments described herein) in combination with at least one non-ionic polymer (according to any of the respective embodiments described herein). In some embodiments, the water-soluble polymers described herein comprise at least one mucin and/or lubricin biopolymer (according to any of the respective embodiments described herein) in combination with at least one non-ionic polymer (according to any of the respective embodiments described herein).

In some embodiments of any of the embodiments described herein, the water-soluble polymers described herein comprise at least one biopolymer (according to any of the respective embodiments described herein) in combination with at least one ionic polymer (according to any of the respective embodiments described herein). In some embodiments, the water-soluble polymers described herein comprise at least one mucin and/or lubricin biopolymer (according to any of the respective embodiments described herein) in combination with at least one ionic polymer (according to any of the respective embodiments described herein).

In some embodiments of any of the embodiments described herein, the water-soluble polymers described herein comprise at least one ionic polymer (according to any of the respective embodiments described herein) in combination with at least one non-ionic polymer (according to any of the respective embodiments described herein).

In some embodiments of any one of the embodiments described herein, a molecular weight (i.e., average molecular weight or Mw, as known in the art) of the water-soluble polymer(s) is in a range of from 3 kDa to 10 MDa. In some embodiments, the molecular weight is from 10 kDa to 10 MDa. In some embodiments, the molecular weight is from 20 kDa to 5 MDa. In some embodiments, the molecular weight Mw is from 30 kDa to 2.5 MDa.

In some embodiments of any one of the embodiments described herein, a molecular weight (i.e., average molecular weight or Mw) of the water-soluble polymer(s) is in a range of from 10 kDa to 1 MDa. In some embodiments, the molecular weight Mw is from 20 kDa to 500 kDa. In some embodiments, the molecular weight Mw is from 30 kDa to 250 kDa. In some embodiments, the water-soluble polymer(s) comprises a non-ionic polymer (according to any of the respective embodiments described herein) having an aforementioned molecular weight. In some embodiments, the non-ionic polymer is PVP and/or PEO having an aforementioned molecular weight.

In some embodiments of any one of the embodiments described herein, a molecular weight (i.e., average molecular weight or Mw) of the water-soluble polymer(s) is in a range of from 0.05 to 10 MDa. In some embodiments, the molecular weight Mw is from 0.05 to 5 MDa. In some embodiments, the molecular weight Mw is from 0.5 to 10 MDa. In some embodiments, the molecular weight Mw is from 0.5 to 5 MDa. In some embodiments, the water-soluble polymer(s) comprises an ionic polymer (according to any of the respective embodiments described herein), optionally an ionic polysaccharide, having an aforementioned molecular weight. In some embodiments, the ionic polymer is hyaluronic acid having an aforementioned molecular weight.

In some embodiments, a concentration of a water-soluble polymer in the solution (according to any of the respective embodiments described herein) is in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the water-soluble polymer is PVP, PEO and/or an ionic polymer and/or polysaccharide (e.g., as described herein in any one of the respective embodiments), optionally hyaluronic acid.

In some embodiments, a concentration of each water-soluble polymer in the solution (according to any of the respective embodiments described herein) is in a range of from 0.01 to 10 mg/ml. In some embodiments, the concentration is in a range of from 0.03 to 10 mg/ml. In some embodiments, the concentration is in a range of from 0.1 to 10 mg/ml. In some embodiments, the concentration is in a range of from 0.3 to 10 mg/ml. In some embodiments, the water-soluble polymer is PVP, PEO and/or hyaluronic acid.

In some embodiments, a total concentration of water-soluble polymer(s) in the solution (according to any of the respective embodiments described herein) is in a range of from 0.01 to 20 mg/ml. In some embodiments, the total concentration is in a range of from 0.03 to 20 mg/ml. In some embodiments, the total concentration is in a range of from 0.1 to 10 mg/ml. In some embodiments, the total concentration is in a range of from 0.3 to 10 mg/ml.

In some embodiments, a concentration of a water-soluble polymer in the solution (according to any of the respective embodiments described herein) is in a range of from 0.01 to 1 mg/ml. In some embodiments, the concentration is in a range of from 0.03 to 1 mg/ml. In some embodiments, the concentration is in a range of from 0.1 to 1 mg/ml. In some embodiments, the concentration is in a range of from 0.3 to 1 mg/ml. In some embodiments, the water-soluble polymer is PVP, PEO and/or an ionic polymer and/or polysaccharide (e.g., as described herein in any one of the respective embodiments), optionally hyaluronic acid.

In some embodiments, a concentration of each water-soluble polymer in the solution (according to any of the respective embodiments described herein) is in a range of from 0.01 to 1 mg/ml. In some embodiments, the concentration is in a range of from 0.03 to 1 mg/ml. In some embodiments, the concentration is in a range of from 0.1 to 1 mg/ml. In some embodiments, the concentration is in a range of from 0.3 to 1 mg/ml. In some embodiments, the water-soluble polymer is PVP, PEO and/or hyaluronic acid.

In some embodiments, a total concentration of water-soluble polymer(s) in the solution (according to any of the respective embodiments described herein) is in a range of from 0.01 to 2 mg/ml. In some embodiments, the total concentration is in a range of from 0.03 to 2 mg/ml. In some embodiments, the total concentration is in a range of from 0.1 to 1 mg/ml. In some embodiments, the total concentration is in a range of from 0.3 to 1 mg/ml.

In some embodiments, a concentration of a water-soluble polymer in the solution (according to any of the respective embodiments described herein) is in a range of from 0.01 to 3 mg/ml. In some embodiments, the concentration is in a range of from 0.01 to 1 mg/ml. In some embodiments, the concentration is in a range of from 0.01 to 0.3 mg/ml. In some embodiments, the concentration is in a range of from 0.01 to 0.1 mg/ml. In some embodiments, the water-soluble polymer is PVP, PEO and/or hyaluronic acid.

In some embodiments, a concentration of each water-soluble polymer in the solution (according to any of the respective embodiments described herein) is in a range of from 0.01 to 3 mg/ml. In some embodiments, the concentration is in a range of from 0.01 to 1 mg/ml. In some embodiments, the concentration is in a range of from 0.01 to 0.3 mg/ml. In some embodiments, the concentration is in a range of from 0.01 to 0.1 mg/ml. In some embodiments, the water-soluble polymer is PVP, PEO and/or hyaluronic acid.

In some embodiments, a total concentration of water-soluble polymer(s) in the solution (according to any of the respective embodiments described herein) is in a range of from 0.01 to 6 mg/ml. In some embodiments, the total concentration is in a range of from 0.01 to 2 mg/ml. In some embodiments, the total concentration is in a range of from 0.01 to 0.6 mg/ml. In some embodiments, the total concentration is in a range of from 0.01 to 0.2 mg/ml.

In some embodiments of any one of the embodiments described herein, the water soluble polymer(s) comprises hyaluronic acid, PVP and/or PEO at a concentration of less than 3 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml. In some embodiments, the hyaluronic acid, PVP and/or PEO is at least 0.3 mg/ml.

In some embodiments of any one of the embodiments described herein, the water soluble polymer(s) comprises hyaluronic acid, PVP and/or PEO at a concentration of less than 0.75 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml. In some embodiments, the hyaluronic acid, PVP and/or PEO concentration is at least 0.3 mg/ml.

In some embodiments of any one of the embodiments described herein, the water soluble polymer(s) comprises hyaluronic acid, PVP and/or PEO at a concentration of less than 0.5 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml. In some embodiments, the hyaluronic acid, PVP and/or PEO concentration is at least 0.3 mg/ml.

In some embodiments of any one of the embodiments described herein, the water soluble polymer(s) comprises hyaluronic acid, PVP and/or PEO at a concentration of less than 0.25 mg/ml. In some embodiments, the hyaluronic acid, PVP and/or PEO acid concentration is at least 0.01 mg/ml. In some embodiments, the hyaluronic acid, PVP and/or PEO concentration is at least 0.03 mg/ml. In some embodiments, the hyaluronic acid, PVP and/or PEO concentration is at least 0.1 mg/ml.

In some embodiments of any one of the embodiments described herein, the water soluble polymer(s) comprises hyaluronic acid, PVP and/or PEO at a concentration of less than 0.1 mg/ml. In some embodiments, the hyaluronic acid, PVP and/or PEO concentration is at least 0.01 mg/ml. In some embodiments, the hyaluronic acid, PVP and/or PEO concentration is at least 0.03 mg/ml.

In some embodiments of any one of the embodiments described herein, a viscosity of the solution (which may reflect at least in part a concentration of water-soluble polymer(s) therein) is no more than 1000 cP (centipoise). In some embodiments, the viscosity is no more than 500 cP. In some embodiments, the viscosity is no more than 200 cP. In some embodiments, the viscosity is no more than 100 cP. In some embodiments, the viscosity is no more than 50 cP. In some embodiments, the viscosity is no more than 20 cP. In some embodiments, the viscosity is no more than 10 cP. In some embodiments, the viscosity is no more than 5 cP. In some embodiments, the viscosity is no more than 3 cP. In some embodiments, the viscosity is no more than 2 cP. In some embodiments, the solution is an aqueous solution having a viscosity described herein.

Herein, viscosities of a solution are determined at a temperature of 20° C. and at a shear rate of 1 second$^{-1}$ (unless indicated otherwise).

Contact Lens:

In some of any one of the embodiments described herein which relate to a contact lens, according to any one of the aspects described herein, the contact lens comprises a hydrogel surface. In some embodiments, the contact lens comprises a hydrogel surface and a rigid center. In some embodiments, the contact lens consists essentially of a hydrogel.

The hydrogel may comprise any material known in the art for use in contact lens hydrogels. Examples of such hydrogel materials include, without limitation, alphafilcon A, asmofilcon A, balafilcon A, bufilcon A, comfilcon A, crofilcon, deltafilcon A, dimefilcon, droxifilcon A, enfilcon A, etafilcon A, galyfilcon A, hefilcon A, hefilcon B, hilafilcon A, hilafilcon B, hioxifilcon A, hioxifilcon D, isofilcon, lidofilcon A, lidofilcon B, lotrafilcon B, mafilcon, methafilcon A, methafilcon B, narafilcon A, narafilcon B, ocufilcon A, ocufilcon B, ofilcon A, omafilcon A, perfilcon, phemfilcon A, polymacon, scafilcon A, senofilcon A, surfilcon, tefilcon, tetrafilcon A, tetrafilcon B, vifilcon A, and xylofilcon A.

In some embodiments of any one of the embodiments described herein, the hydrogel comprises a polymer selected from the group consisting of poly(2-hydroxyethyl methacrylate) and a silicone. In some embodiments, the polymer comprises a silicone. Such polymers may optionally comprise small amounts of additional monomers (e.g., cross-linking monomers) copolymerized with the 2-hydroxyethyl methacrylate or silicone monomer. For example, 2-hydroxyethyl methacrylate may optionally be copolymerized with vinyl pyrrolidone, methyl methacrylate, methacrylic acid (an anionic monomer), ethylene glycol dimethacrylate (a cross-linking monomer) and/or 3-(ethyldimethyl-ammonium)propyl methacrylamide (a cationic monomer) in a contact lens hydrogel.

In some embodiments of any one of the embodiments described herein, the contact lens surface material (e.g., polymer) is not capable of selective binding to the water-soluble polymer(s) according to any of the respective embodiments described herein (e.g., hyaluronic acid, PVP and/or PEO).

In some embodiments of any one of the embodiments described herein, the water-soluble polymer(s) according to any of the respective embodiments described herein (e.g., hyaluronic acid, PVP and/or PEO) binds to the contact lens surface by non-specific adsorption.

In some embodiments of any one of the embodiments described herein, the contact lens surface material (e.g., polymer) is capable of selective binding to the water-soluble polymer(s) according to any of the respective embodiments described herein. In some such embodiments, the water-soluble polymer(s) comprises an ionic polymer according to any of the respective embodiments described herein (e.g., hyaluronic acid). In some embodiments, the contact lens surface is a modified surface, selected to be capable of selective binding to the water-soluble polymer(s) (e.g., hyaluronic acid).

In some embodiments of any one of the embodiments described herein, the contact lens surface is not modified in a manner which enhances attachability of the water-soluble polymer(s) to the surface.

In some embodiments of any one of the embodiments described herein, the water-soluble polymer(s) (e.g., non-modified hyaluronic acid, PVP and/or PEO) is not modified in a manner which enhances attachability of the water-soluble polymer(s) to the surface.

In some embodiments of any one of the embodiments described herein, the hydrogel consists essentially of a polymer and an aqueous liquid (optionally water).

In some embodiments of any one of the embodiments described herein, the hydrogel in the contact lens comprises a polymer having no more than 2 charged groups per kDa of polymer. In some embodiments, the polymer has no more than 1 charged group per kDa. In some embodiments, the polymer has no more than 0.5 charged group per kDa. In some embodiments, the polymer has no more than 0.2 charged group per kDa. In some embodiments, the polymer has no more than 0.1 charged group per kDa.

In some embodiments of any one of the embodiments described herein, the hydrogel in the contact lens comprises a polymer having no more than 2 negatively charged groups per kDa of polymer. In some embodiments, the polymer has no more than 1 negatively charged group per kDa. In some embodiments, the polymer has no more than 0.5 negatively charged group per kDa. In some embodiments, the polymer has no more than 0.2 negatively charged group per kDa. In some embodiments, the polymer has no more than 0.1 negatively charged group per kDa.

In some embodiments of any one of the embodiments described herein, the hydrogel in the contact lens comprises a polymer having a net charge of no more than 2 electric charges per kDa of polymer. In some embodiments, the polymer has a net charge of no more than 1 charge per kDa. In some embodiments, the polymer has a net charge of no more than 0.5 charge per kDa. In some embodiments, the polymer has a net charge of no more than 0.2 charge per kDa. In some embodiments, the polymer has a net charge of no more than 0.1 charge per kDa. In some embodiments, the net charge is a negative net charge.

Without being bound by any particular theory, it is believed that a relatively low level of charged groups and/or net charge may be advantageous when the polymer of the hydrogel has a net charge having the same sign as a net charge of a water-soluble polymer(s) which comprises an ionic polymer (according to any of the respective embodiments described herein), in order to minimize electrostatic repulsion between the ionic polymer described herein and the hydrogel.

In some embodiments of any one of the embodiments described herein, the contact lens comprises a surface which is positively charged or neutrally charged, that is, the net charge is not a negative net charge. In some such embodiments, the liposomes are characterized by a positive surface charge (e.g., liposomes comprising phosphatidylcholine, as described herein in any one of the respective embodiments). In such embodiments, there is typically no significant electrostatic attraction between the liposomes and the contact lens surface, and thus the water-soluble polymer(s) described herein may be particularly useful for mediating adherence of the liposome lipids to the lens surface.

In some embodiments of any one of the embodiments described herein, the contact lens comprises a surface which is negatively charged or neutrally charged, that is, the net charge is not a positive net charge. In some such embodiments, the liposomes are characterized by a negative surface charge. In such embodiments, there is typically no significant electrostatic attraction between the liposomes and the contact lens surface, and thus the water-soluble polymer(s) described herein may be particularly useful for mediating adherence of the liposome lipids to the lens surface.

Carrier and Formulation:

In some embodiments of any one of the embodiments described herein, the carrier is an ophthalmically acceptable carrier. In some such embodiments, the solution can be allowed to remain on the contact lens following rinsing and/or immersing in the solution, as the residual solution will not harm the eye when the contact lens is placed on the eye.

Herein, the phrase "ophthalmically acceptable carrier" refers to a carrier or a diluent that does not cause significant irritation to a subject when contacted with an eye (e.g., cornea and/or sclera) of the subject, and does not abrogate the activity and properties of the water-soluble polymer(s) and liposomes in the solution (e.g., their ability to reduce a friction coefficient of a contact lens surface).

In some embodiments of any one of the embodiments described herein, the carrier is not an ophthalmically acceptable carrier. Examples of such carriers include, without limitation, carriers comprising a preservative and/or a concentration of preservative which is not ophthalmically acceptable. Such carriers may be suitable, for example, for immersing a contact lens for an extended period of time, and/or for storage for an extended period of time, while limiting the risk of bacterial growth in the solution. Typically, a solution comprising such a carrier is rinsed with an ophthalmically acceptable liquid (e.g., water, saline) solution prior to placing the contact lens on the eye.

In some embodiments of any one of the embodiments described herein, the solution is formulated as a solution suitable for storage of contact lenses (e.g., soft contact lenses), for example, as known in the art. Examples of ingredients suitable for such solutions, which may be optionally included in the solution according to some embodiments of the invention, include, without limitation, buffers (e.g., borate and/or phosphate, having a pH of from about 6.5 to 7.6), wettability enhancers and humectants (optionally additional water-soluble polymers such as polyvinyl alcohol and/or hydroxypropylmethylcellulose).

Techniques for formulation and administration of compounds may be found in "Remington's Pharmaceutical Sciences" Mack Publishing Co., Easton, PA, latest edition, which is incorporated herein by reference.

Solutions according to any one of the embodiments of the present invention may be manufactured by processes well known in the art, e.g., by means of conventional mixing or dissolving processes.

Solutions for use in accordance with the present invention thus may be formulated in conventional manner using one or more ophthalmically acceptable carriers, which facilitate processing of the water-soluble polymer(s) and/or liposomes into preparations which can be used as described herein. The water-soluble polymer(s) and/or liposomes described herein may be formulated as an aqueous solution per se. Additionally, the solution may be in the form of a suspension and/or emulsions (e.g., the aqueous phase of a suspension or water-in-oil, oil-in-water or water-in-oil-in-oil emulsion), for example, in order to increase the viscosity of the formulation.

In some embodiments, the water-soluble polymer(s) and/or liposomes described herein may be in powder form for constitution with a suitable vehicle such as water, e.g., sterile, pyrogen-free water, before use.

The solutions may be formulated wherein the active ingredient(s) (water-soluble polymer(s) and/or liposomes) are contained in an amount effective to achieve the intended purpose, for example, an amount effective to prevent, alleviate or ameliorate symptoms of a disorder in the subject being treated.

The amount of a composition to be administered will, of course, be dependent on the subject being treated, the severity of the affliction, the manner of administration, the judgment of the prescribing physician, etc.

Kits and Articles:

According to another aspect of embodiments of the invention, there is provided a kit comprising at least one contact lens; and a solution for use in rinsing and/or immersing therein a contact lens and/or for use in treatment of ocular discomfort, according to any one of the embodiments described herein.

Typically, the kit will comprise at least two contact lenses, e.g., at least one pair of contact lenses.

In some embodiments of any one of the embodiments described herein, the kit comprises at least 6 contact lenses. In some embodiments, the kit comprises at least 10 contact lenses. In some embodiments, the kit comprises at least 20 contact lenses. In some embodiments, the kit comprises at least 30 contact lenses. In some embodiments, the kit comprises at least 50 contact lenses. In some embodiments, the kit comprises at least 100 contact lenses.

In some embodiments of any one of the embodiments described herein, the kit comprises a plurality of packaging units (e.g., blister packs), each packaging unit comprising one contact lens.

In some embodiments of any one of the embodiments described herein, the kit comprises a plurality of packaging units (e.g., blister packs), each packaging unit comprising one pair of contact lenses.

In some embodiments of any one of the embodiments described herein, a contact lens in the kit is immersed in a solution. In some embodiments, the contact lens is a soft contact lens, and the solution is a solution suitable for storage of soft contact lenses, for example, as known in the art. The solution may optionally be the solution according to some embodiments of the invention, or a different solution, for example, a standard solution for storage of contact lenses.

In some embodiments of any one of the embodiments described herein, the at least one contact lens in the kit is immersed in the solution comprising liposomes and water-soluble polymer, as described herein in any one of the respective embodiments, for example, packaged in a packaging unit (e.g., blister pack) containing the solution.

Without being bound by any particular theory, it is believed that packaging a contact lens immersed in the solution comprising liposomes and water-soluble polymer provides ample time for the water-soluble polymer(s) and liposome lipids to coat the contact lens surface, as described herein in any one of the respective embodiments, and avoids the need for a user of the kit to contact the contact lens with the solution.

In some embodiments of any one of the embodiments described herein, the solution is formulated as a solution suitable for storage of contact lenses (e.g., soft contact lenses), according to any of the respective embodiments described herein.

In some embodiments of any one of the embodiments described herein, the at least one contact lens and the solution comprising liposomes and water-soluble polymer(s), as described herein in any one of the respective embodiments, are packaged separately within the kit. In such embodiments, the at least one contact lens may optionally be immersed in a solution other than the solution comprising liposomes and water-soluble polymer(s), or not be immersed in any solution. In some embodiments, the solution comprising liposomes and water-soluble polymer(s), as described herein in any one of the respective embodiments, is packaged in a container configured for dispensing the solution, optionally configured for dispensing a predetermined volume of the solution. In some embodiments, the kit includes instructions for rinsing a contact lens with the solution and/or immersing a contact lens in the solution (e.g., for a predetermined period of time) prior to wearing the contact lens, to thereby reduce the friction coefficient of the contact lens surface prior to wearing.

According to another aspect of embodiments of the invention, there is provided an article-of-manufacturing comprising the solution described herein for use in rinsing and/or immersing therein a contact lens, and/or for use in treatment of ocular discomfort. According to this aspect, the solution is packaged in a container configured for dispensing the solution. Examples of such containers include, without limitation, squeezable containers configured for dispensing the solution upon squeezing the container, spray containers configures for dispensing the solution as an aerosol and/or a liquid jet, containers configured for dispensing the solution slowly (e.g., as discrete drops), and metered-dose containers configured for dispensing a predetermined amount of solution.

In some embodiments, the container is configured for dispensing a predetermined volume of the solution (e.g., a predetermined volume in a range of from 0.5 to 20 ml, optionally from 1 to 10 ml).

Solutions (or formulations) according to embodiments of the present invention may, if desired, be presented in a pack or dispenser device (e.g., as described herein), such as an FDA (the U.S. Food and Drug Administration) approved kit, which may contain one or more unit dosage forms containing the active ingredient(s) (e.g., water-soluble polymer(s) and/or liposomes described herein). The pack may, for example, comprise metal or plastic foil, such as, but not limited to a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Solutions comprising water soluble polymer(s) and/or liposomes, as described herein in any one of the respective embodiments, formulated in an ophthalmically acceptable carrier may also be prepared, placed in an appropriate container, and labeled for treatment of an indicated condition or diagnosis, as is detailed herein.

Additional Definitions

Herein, the term "alkyl" describes a saturated or unsaturated aliphatic hydrocarbon including straight chain and branched chain groups. Preferably, the alkyl group has 1 to 20 carbon atoms. Whenever a numerical range; e.g., "1 to 20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. Substituted alkyl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine.

When unsaturated, an alkyl may comprise at least one carbon-carbon double bond, in which case it may also be referred to as an "alkenyl", and/or at least one carbon-carbon triple bond, in which case it may also be referred to as an "alkynyl".

The alkyl group can be an end group, as this phrase is defined herein, wherein it is attached to a single adjacent atom, or a linking group, as this phrase is defined herein, which connects two or more moieties.

Herein, the phrase "end group" describes a group (e.g., a substituent) that is attached to a single moiety in the compound via one atom thereof.

The phrase "linking group" describes a group (e.g., a substituent) that is attached to two or more moieties in the compound.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or non-substituted. Substituted cycloalkyl may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The cycloalkyl group can be an end group, as this phrase is defined herein, wherein it is attached to a single adjacent atom, or a linking group, as this phrase is defined herein, connecting two or more moieties.

The term "aryl" describes an all-carbon monocyclic or fused-ring polycyclic (i.e., rings which share adjacent pairs of carbon atoms) groups having a completely conjugated pi-electron system. The aryl group may be substituted or non-substituted. Substituted aryl may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The aryl group can be an end group, as this term is defined herein, wherein it is attached to a single adjacent atom, or a linking group, as this term is defined herein, connecting two or more moieties.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. Substituted heteroaryl may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The heteroaryl group can be an end group, as this phrase is defined herein, where it is attached to a single adjacent atom, or a linking group, as this phrase is defined herein, connecting two or more moieties. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. Substituted heteroalicyclic may have one or more substituents, whereby each substituent group can independently be, for example, alkyl, cycloalkyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carboxy, thiocarbamate, urea, thiourea, carbamate, amide, and hydrazine. The heteroalicyclic group can be an end group, as this phrase is defined herein, where it is attached to a single adjacent atom, or a linking group, as this phrase is defined herein, connecting two or more moieties. Representative examples are piperidine, piperazine, tetrahydrofuran, tetrahydropyran, morpholine and the like.

As used herein, the terms "amine" and "amino" describe both a —NRxRy group —NRx- group, wherein Rx and Ry are each independently hydrogen, alkyl, cycloalkyl, aryl, heteroaryl or heteroalicyclic, as these terms are defined herein. When Rx or Ry is heteroaryl or heteroalicyclic, the amine nitrogen atom is bound to a carbon atom of the heteroaryl or heteroalicyclic ring.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of Rx and Ry is independently alkyl, cycloalkyl, aryl, heteroaryl or heteroalicyclic.

The terms "halide" and "halo" refer to fluorine, chlorine, bromine or iodine.

The term "haloalkyl" describes an alkyl group as defined herein, further substituted by one or more halide(s).

The term "phosphonate" refers to an —P(=O)(ORx)-$OR_Y$ end group, or to a —P(=O)(ORx)-O— linking group, where Rx and $R_Y$ are as defined herein.

The term "sulfoxide" or "sulfinyl" describes a —S(=O)—Rx end group or —S(=O)— linking group, where Rx is as defined herein.

The terms "sulfonate" and "sulfonyl" describe a —S(=O)$_2$—Rx end group or —S(=O)$_2$— linking group, where Rx is as defined herein.

The term "sulfonamide", as used herein, encompasses both S-sulfonamide and N-sulfonamide end groups, and a —S(=O)$_2$—NRx- linking group.

The term "S-sulfonamide" describes a —S(=O)$_2$—NRx$R_Y$ end group, with Rx and $R_Y$ as defined herein.

The term "N-sulfonamide" describes an RxS(=O)$_2$—$NR_Y$— end group, where Rx and $R_Y$ are as defined herein.

The term "carbonyl" as used herein, describes a —C(=O)—Rx end group or —C(=O) linking group, with Rx as defined herein.

The term "acyl" as used herein, describes a —C(=O)—Rx end group, with Rx as defined herein.

The terms "hydroxy" and "hydroxyl" describe a —OH group.

The term "alkoxy" describes both an —O-alkyl and an —O-cycloalkyl end group or linking group, as defined herein.

The term "aryloxy" describes both an —O-aryl and an —O-heteroaryl end group or linking group, as defined herein.

The term "thiohydroxy" describes a —SH group.

The term "thioalkoxy" describes both a —S-alkyl end group or linking group, and a —S-cycloalkyl end group or linking group, as defined herein.

The term "thioaryloxy" describes both a —S-aryl and a —S-heteroaryl end group or linking group, as defined herein.

The terms "cyano" and "nitrile" describe a —CN group.

The term "nitro" describes an —NO$_2$ group.

The term "azo" describes an —N=N-Rx end group or —N=N= linking group, with Rx as defined herein.

The terms "carboxy" and "carboxyl", as used herein, encompasses both C-carboxy and O-carboxy end groups, and a —C(=O)—O— linking group.

The term "C-carboxy" describes a —C(=O)—ORx end group, where Rx is as defined herein.

The term "O-carboxy" describes a —OC(=O)—Rx end group, where Rx is as defined herein.

The term "urea" describes a —NRxC(=O)—NRyRw end group or —NRxC(=O)—NRy- linking group, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The term "amide", as used herein, encompasses both C-amide and N-amide end groups, and a —C(=O)—NRx- linking group.

The term "C-amide" describes a —C(=O)—NRxRy end group, where Rx and Ry are as defined herein.

The term "N-amide" describes a RxC(=O)—NRy- end group, where Rx and Ry are as defined herein.

The term "carbamyl" or "carbamate", as used herein, encompasses N-carbamate and O-carbamate end groups, and a —OC(=O)—NRx- linking group.

The term "N-carbamate" describes an RyOC(=O)—NRx- end group, with Rx and Ry as defined herein.

The term "O-carbamate" describes an —OC(=O)—NRxRy end group, with Rx and Ry as defined herein.

The term "thiocarbamyl" or "thiocarbamate", as used herein, encompasses both O-thiocarbamate, S-thiocarbamate and N-thiocarbamate end groups, and a —OC(=S)—NRx- or —SC(=O)—NRx- linking group.

The term "O-thiocarbamate" describes a —OC(=S)—NRxRy end group, with Rx and Ry as defined herein.

The term "S-thiocarbamate" describes a —SC(=O)—NRxRy end group, with Rx and Ry as defined herein.

The term "N-thiocarbamate" describes an RyOC(=S)NRx- or RySC(=O)NRx-end group, with Rx and Ry as defined herein.

The term "guanidine" describes a —RxNC(=N)—NRyRw end group or —RxNC(=N)—NRy- linking group, where Rx, Ry and Rw are as defined herein.

The term "hydrazine", as used herein, describes a —NRx-NRyRw end group or —NRx-NRy- linking group, with Rx, Ry, and Rw as defined herein.

As used herein the term "about" refers to ±10%, and optionally ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Hyaluronic acid (sodium hyaluronate, 1 and 1.5 MDa) was obtained from Lifecore Biomedical.

Phosphate buffer saline (PBS) was obtained from Sigma-Aldrich.

Phosphatidylcholines (PC), including dimyristoylphospatidylcholine (1,2-dimyristoyl-sn-glycero-3-phosphocholine; DMPC) and hydrogenated soy PC (HSPC), were obtained from Lipoid GmbH.

Polyethylene glycol (PEG or PEO), 200 kDa molecular weight, was obtained from Sigma-Aldrich.

Polyvinylpyrrolidone (PVP), 40 kDa molecular weight, was obtained from Sigma-Aldrich.

Etafilcon A (1-Day ACUVUE®) and Narafilcon A (1-Day TruEye®) contact lenses were obtained from Johnson & Johnson, immersed in saline solution in a blister-pack. The composition, water content and modulus of the contact lenses are as follows. Etafilcon A lenses contain 2-hydroxyethylmethacrylate (HEMA) and methacrylic acid (MA), have a water content of 58%, and a modulus of 0.3 MPa. Narafilcon A lenses contain silicone, have a water content of 46%, and a modulus of 0.66 MPa.

A saline commercial lens cleaning fluid (Sensitive Eyes® Plus saline solution) was obtained from Bausch & Lomb, and is referred to herein as "B&L saline".

Water used was purified by Barnsted NanoPure systems to a resistance of 18.2 MΩ-cm resistance with total organic content levels of less than approximately 1 part per billion.

Liposome Preparation (Multilamellar Vesicles):

Multilamellar vesicles (MLV) composed either of dimyristoylphosphatidylcholine (1,2-dimyristoyl-sn-glycero-3-phosphocholine; DMPC) or of hydrogenated soy PC (HSPC) were prepared by hydrating the lipids at a temperature at least 5° C. above the lipid melting point ($T_M$), followed by sonication, in phosphate buffer saline (PBS). Where MLV liposomes were mixed with hyaluronic acid (HA), the polymer solution (in PBS) was prepared in advance, and after full dissolution of the HA, the solution was warmed to a temperature at least 5° C. above the lipid $T_M$, and added to the lipids, followed by stirring to mix.

Liposome Preparation (Small Unilamellar Vesicles):

Multilamellar vesicles (MLV) composed of dimyristoylphosphatidylcholine (DMPC) or hydrogenated soy PC (HSPC) were prepared by hydrating the lipids at a temperature above the lipid melting point ($T_M$), according to the procedures described hereinabove. In order to obtain small unilamellar vesicles (SUV), the MLVs were downsized by stepwise extrusion through polycarbonate membranes, starting with a 400 nm and ending with 50 nm pore size membrane, using a Lipex 100 mL extruder system (Northern Lipids, Vancouver, Canada), at a temperature above the lipid $T_M$.

Where SUV liposomes were mixed with a polymer, the polymer solution (in PBS) was prepared in advance, and after full dissolution of the polymer, the polymer solution was added to the lipids, followed by stirring to mix for 2 hours.

Multilamellar vesicles and small unilamellar vesicles composed of other pure phosphatidylcholines, such as dipalmitoylphosphatidylcholine (DPPC), dilauroylphosphatidylcholine (DLPC) and/or distearoylphosphatidylcholine (DSPC), according to the procedures described hereinabove.

Friction Measurements:

Friction tests were performed with a UMT model tribometer (Bruker). Contact lenses were mounted on a cornea-mimicking holder, which has a typical geometry resembling the human cornea, as shown in FIGS. 1A and 1B. The contact lens was then positioned opposite a glass plate and immersed in B&L saline (Example 1) or PBS (Example 2) during the measurement. The normal loads used were 3 grams, 5 grams, 10 grams and 40 grams.

The friction coefficient was calculated by dividing the measured lateral force during sliding by the applied normal force. Friction coefficient values are those of kinetic friction, which is related to the forces in the system that are measured when there is a sliding motion of the contact lens on the opposing glass surface. Parameters were as follows: sliding velocity 1 mm per second, frequency 1 Hz, and dwell time of 5 seconds prior to initiation of motion. Experiments were conducted at a temperature of 36±0.5° C. (Example 1) or 37±1° C. (Example 2).

Each friction coefficient value (μ) is an average of friction measurements for at least 5 different etafilcon A (HEMA/MA) lenses, or for at least 3 different narafilcon A (silicone)

lenses, for each immersion condition. Moreover, each friction measurement is an average over 180 cycles for each of 2 to 3 different contact position on the glass surface. The same glass surface was used for one entire set of experiments for a given lens type, and the order of measurements was as follows: first, saline controls; then a lens that had been immersed in HA; then a lens that had been immersed in HSPC; then a lens that had been immersed in HSPC+HA; then a lens that had been immersed in DMPC; then a lens that had been immersed in DMPC+HA. Between each different lens the B&L saline or PBS immersing the lens/substrate system was replaced by fresh B&L saline or PBS, respectively. The glass surface was then changed, and the measurements repeated (5 times for etafilcon A and 3 times for narafilcon A).

In one case, following the full set of measurements with a given glass substrate, the measurement for the (HSPC+HA)-immersed lens on the same substrate was repeated, and the earlier measured value (for the same (HSPC+HA)-immersed lens) was reproduced.

The mean pressure P over the contact area A was determined according to the equation: $P=F_N/A$, where FN is the applied normal load and, from Hertzian contact mechanics [Johnson, K. L., *Contact Mechanics* 2004, London: Cambridge University Press], $A=\pi(RF_N/K)^{2/3}$, where R is the radius of the rigid cornea-mimicking holder and K is the Young's modulus of the contact lens.

Dynamic Light Scattering (DLS):

Dynamic light scattering (DLS) measurements of the various suspensions were determined using a ZetaSizer μV apparatus (Malvern Instruments).

Example 1

Hyaluronic Acid Lubrication Solutions

Lenses were removed from their blister-pack, where they had been immersed in a saline solution, and were then immersed for 2 days in either an HA solution in PBS, a liposome solution in PBS, or a combined HA+liposome solution in PBS. Immersion was carried out in the original blister-pack to which the immersing solution was added after removing the original saline. For the control measurements where lenses were not immersed in one of the solutions, the lenses were used immediately following removal from their original blister pack.

Prior to measurements in the tribometer, in all samples (including the controls), the lenses were thoroughly rinsed by a stream of B&L saline. The lenses were then mounted on the tribometer holder and friction forces measured while sliding against a glass surface and immersed in B&L saline.

The glass substrates used were thin 24 mm×24 mm coverglasses (Knittel Glaser, Germany). They were removed from their pack (edge-handled with latex gloves throughout), and glued into a standard 35 mm diameter polystyrene Petri dish using Devcon® 5 Minute® 2-component epoxy. Just prior to the friction measurements, the upper glass surface was wiped with an ethanol-moistened Kimwipes® tissue, then rinsed in de-ionized water to remove any ethanol traces, and the Petri dish then filled with B&L saline.

Results:

Dynamic light scattering (DLS) measurements showed that HA in PBS had a hydrodynamic diameter of 135±20 nm. For the MLV HSPC and DMPC liposomes in PBS solution, DLS measurements yielded diameters of 3±1.5 μm and 1.4±0.7 μm, respectively.

DLS measurements of the MLV's HSPC and DMPC liposomes mixtures with HA indicated diameters of 2.5±1.5 μm and 2.8±1.5 μm, respectively.

Friction coefficients were measured in B&L saline environment either following removal of the lens from the blister-pack and rinsing in B&L saline (labeled 'saline' in the figure legends), or following immersion in PBS solutions containing the tested liposomes (at a concentration of 45 mM) and/or HA (1 M; 0.2 mg/ml), and rinsing in B&L saline, for the two lens types.

The applied loads (L) were 5 grams, 10 grams or 40 grams, and the corresponding mean pressures P (in Atm units) are presented in FIGS. 2 and 3, respectively as L/P.

As shown in FIGS. 2 and 3, the sliding friction coefficients μ of lenses that were only rinsed in B&L saline following removal from their blister-pack, and then slid across a glass slide immersed in B&L saline, was in the range 0.08±0.04 for HEMA hydrogel lenses (Etafilcon A) and 0.2±0.1 for Silicone hydrogel lenses (Narafilcon A). These values are considered as the baseline control relative to the values obtained with other solutions, and are designated herein as $\mu_0$.

As further shown in FIGS. 2 and 3, following immersion in HA solution, the sliding friction coefficient μ decreased relative to the baseline value $\mu_0$, by 30% and 50%, for the Etafilcon A and the Narafilcon A lenses, respectively.

Following immersion in liposome solutions, a significant reduction in the sliding friction coefficient μ relative to $\mu_0$ was generally noted, ranging between 25% to about 75% for the HSPC liposomes and between 65% to 92% for the DMPC liposomes.

Following immersion in the HA/liposome mixtures, substantially higher reduction in sliding friction coefficients μ relative to $\mu_0$ were invariably observed, ranging from about 2-fold reduction for Etafilcon (HEMA) immersed in HA+HSPC to more-than-10-fold reduction for Narafilcon (silicone) immersed in HA+DMPC.

In some cases, the friction coefficients were somewhat lower at the higher loads.

These results present a synergistic effect of a solution containing both HA and liposomes. It is to be understood that in sliding friction coefficient, when two or more lubricants are measured alone and in combination, it is expected that the combination would result in averaged values of the friction coefficient. However, surprisingly, a solution containing HA and the liposomes resulted in friction coefficient values which were substantially lower than the friction coefficient values obtained for either component alone, thus demonstrating a synergistic effect.

It is noted that all measurements were performed following 2-day immersion of the lenses in the tested solutions and a subsequent thorough rinse in a stream of B&L saline, such that subsequent measurements were made in B&L saline alone. It is therefore assumed that there was no trace of free HA or liposomes in the liquid surrounding the lenses in the tribometer.

Some Non-Limiting Mechanistic Insights:

Without being bound by any particular theory, the following provides a tentative explanation of the results presented above.

The reduction in the friction coefficient upon immersion in HA solution and a subsequent rinse in B&L saline may be regarded as evidence of an interaction and possible attachment of the HA to the surface of the hydrogel of the contact lens.

HA is known as an additive to eye-drops and to lens immersion solutions due to its therapeutic properties [Price et al. Journal of Plastic, Reconstructive & Aesthetic Surgery, 2007. 60(10): p. 1110-1119], and is known not to be a good boundary lubricant [Seror et al., *Biomacromolecules*, 13(11):3823-3832, (2012)]; Benz et al. *Journal of Biomedical Materials Research Part A,* 2004. 71A:6-15], although viscous solutions of HA, similarly to other viscous solutions, have been considered to act as non-boundary lubricants [Doughty, *Contact Lens and Anterior Eye* 1999, 22:116-126].

The higher reduction (relative to saline and to HA solutions) in the friction coefficient upon immersion in liposomes solution and a subsequent rinse in B&L saline may be regarded as evidence of coverage of the contact lens hydrogel surface. PC liposomes are well known to act as efficient boundary lubricants, hence the (generally observed) reduction in $\mu$ relative to $\mu_0$.

It is assumed that the low pressures at which measurements were performed, which are lower relative to earlier studies of lubrication by liposomes, the DMPC lipids provide better lubrication than the HSPC, possibly because that at 36° C., the DMPC are in their liquid disordered (LD) phase ($T_M$(DMPC)=24° C.) and hence are more highly hydrated than the HSPC, which at 36° C. is in its solid ordered (SO) phase ($T_M$(HSPC)=53° C.). It is noted that in previous studies, at much high pressures, the situation is reversed, and HSPC liposomes are the better lubricants since their bilayers are more robust than the DMPC ones [Goldberg, R., et al., *Advanced Materials,* 2011, 23:3517-3521; Sorkin, R., et al., *Biomaterials,* 2013. 34:5465-5475].

When the lenses are immersed in a mixture of the liposomes and HA, HA adsorbs on the lenses and, in this surface-attached form, complexes with the lipids to form highly lubricating boundary layers.

These findings are also qualitatively consistent with the somewhat weaker effect that HA has either on its own or, synergistically, with the liposomes, when Etafilcon lenses (HEMA+MA groups) are used relative to Narafilcon (silicone).

The Etafilcon lens is slightly negatively charged due to the methacrylic acid (MA) groups, whereby the Narafilcon is uncharged. HA exhibits both negative charge and hydrophobicity. It is therefore assumed that while HA may interact via hydrophobic and electrostatic interactions, it adheres more weakly to negatively-charged surfaces such as HEMA. This lower absorbance of HA on the Etafilcon accounts for the weaker reduction in friction for Etafilcon vs. Narafilcon, both when HA alone is used, and when it is used together with liposomes in the immersing solutions, thus indicating a role for HA absorbance to the lens surface in reducing friction coefficient and increasing lubricity.

Additional Measurements:

Friction coefficients are measured for contact lenses, according to procedures such as described hereinabove, following immersion in solutions comprising different concentrations of liposomes (e.g., other than the abovementioned 45 mM), different concentrations of HA (e.g., other than the abovementioned 0.2 mg/ml), different types of liposomes (e.g., small unilamellar vesicles) and/or different phospholipids in the liposomes (e.g., dipalmitoylphosphatidylcholine (DPPC), dilauroylphosphatidylcholine (DLPC) and/or distearoylphosphatidylcholine (DSPC)), in order to assess the effect of liposome and/or HA concentration, phospholipid, and/or liposome type on the measured friction coefficient. The concentrations of HA (optionally non-modified HA) are optionally no more than about 1 mg/ml (e.g., within a range of from 0.01 to 1 mg/ml), in order to maintain a liquid nature of the solutions. The liposome concentrations are optionally characterized by a phospholipid concentration in a range of from 0.5 mM to 500 mM.

In addition, friction coefficients are measured for contact lenses, according to any of the procedures described hereinabove, except that the lenses are not rinsed after immersion.

In order to assess the activity of HA (optionally modified HA) and liposomes at the surface of contact lens hydrogels, the HA and/or liposomes are labeled (e.g., by a fluorescent label). Adsorption of HA and/or liposomes onto the surface of the hydrogel is measured by detecting and optionally quantifying levels of labeled HA and/or liposomes at the hydrogel surface. In addition, the effect of HA on liposome adsorption and/or the effect of liposomes on HA adsorption are optionally determined (e.g., quantitatively) by comparing adsorption in the presence of liposomes and HA with adsorption of liposomes without HA and/or HA without liposomes.

HA (optionally modified HA) is optionally labeled by fluorescent labeling (e.g. with fluorescein) or by other approaches, optionally biotin-avidin chemistry, for example, using biotinylated HA (e.g., as described below), and detecting the biotinylated HA by contacting a sample with labeled (e.g., fluorescent-labeled) avidin.

Liposomes are optionally labeled by contact of the phospholipids with a lipophilic marker (e.g., a fluorescent compound), such that the marker is incorporated into the liposome phospholipid layer; by covalently coupling the phospholipids with a lipophilic marker (e.g., a fluorescent compound), optionally 7-nitro-2,1,3-benzoxadiazole (NBD), which may be coupled, for example, to amine groups in a phosphoethanolamine moiety and/or in an amine-substituted fatty acyl moiety; and/or by preparation of the liposomes in a solution of a marker (e.g., a fluorescent compound), such that the marker is entrapped within the liposome.

The HA and liposomes are preferably labeled by readily distinguishable labels (e.g., fluorescent labels with different emission and/or absorption wavelengths), in order to facilitate measurements of each of HA and liposomes in the present of a combination thereof.

Example 2

Additional Lubrication Solutions

Lenses were removed from their container, where they had been immersed in a phosphate buffer saline (PBS) solution, and were rinsed using PBS. The lenses were then immersed for 2 days in a PBS solution of liposomes and/or a polar polymer (hyaluronic acid (HA), polyvinylpyrrolidone (PVP) or polyethylene oxide (PEO)), or in PBS alone (as a control).

Prior to measurements in the tribometer, in all samples, the lenses were thoroughly rinsed by a stream of PBS. The lenses were then mounted on the tribometer holder and friction forces measured while sliding against a glass surface and immersed in PBS.

The glass substrates used were thin 24 mm×24 mm coverglasses (Knittel Glaser, Germany). They were removed from their pack (edge-handled with latex gloves throughout), and glued into a standard 35 mm diameter polystyrene Petri dish using Devcon® 5 Minute® 2-component epoxy. Just prior to the friction measurements, the upper glass surface was wiped with an ethanol-moistened Kimwipes® tissue, then rinsed in de-ionized water to remove any ethanol traces, and the Petri dish then filled with PBS.

Dynamic light scattering (DLS) measurements showed that HSPC SUVs had a diameter of ~100 nm, and DMPC SUVs had a diameter of ~72 nm.

Friction coefficients were measured in PBS environment following immersion for two days in PBS per se or PBS solutions containing the tested liposomes (at a concentration of 10 mM) and/or the tested polymers (0.2 mg/ml).

The applied loads (L) were 3 grams or 10 grams, and the corresponding mean pressures (P) are presented in FIGS. 4-7, respectively as L (in grams)/P (in Atm units).

As shown in FIGS. 4-7, and in Table 1 below, immersion in DMPC (FIGS. 4 and 6) or HSPC (FIGS. 5 and 7) liposome solutions resulted in a significant reduction in the sliding friction coefficient µ of Etafilcon A (FIGS. 4 and 5) and Narafilcon A (FIGS. 6 and 7) lenses relative to lenses immersed in PBS, in accordance with the results described in Example 1.

As further shown in FIGS. 4-7 and in Table 1, immersion in polymer/liposome mixtures generally resulted in substantially higher reduction in sliding friction coefficients µ than did immersion in polymer solution or liposome solution, especially at a load of 10 grams.

It is noted that all measurements were performed following 2-day immersion of the lenses in the tested solutions and a subsequent thorough rinse in a stream of PBS, such that subsequent measurements were made in PBS alone. It is therefore assumed that there was no trace of free polymer or liposomes in the liquid surrounding the lenses in the tribometer. Thus, the results indicate an interaction and possible attachment of the polymers to the surface of the hydrogel of the contact lens.

Without being bound by any particular theory, it is believed that results at a load of 10 grams are more representative of long-term lubrication effects than are results at a load of 3 grams.

As shown in FIG. 4 and in Table 1, PVP/DMPC liposome and PEO/DMPC liposome mixtures resulted in a reduction of 50% or more in the friction coefficients of Etafilcon A lenses in comparison with DMPC liposomes alone at a load of 10 grams.

Figure 5:
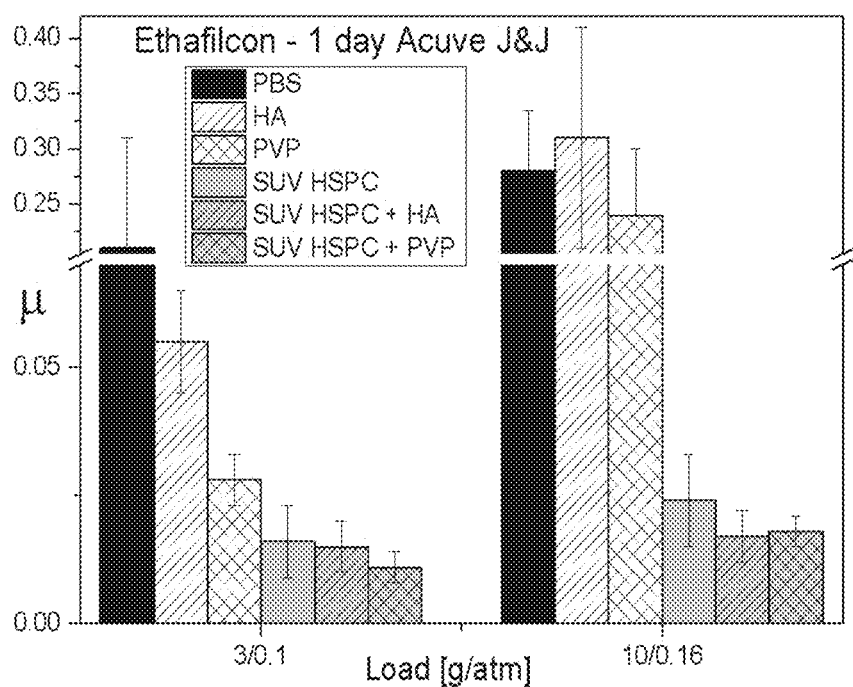
FIG. 5 presents bar graphs showing the friction coefficient of Etafilcon A contact lens upon immersion in PBS, solutions of HA or PVP (0.2 mg/ml), a solution of SUV HSPC liposomes (10 mM), or solutions of SUV HSPC liposomes with HA or PVP, followed by rinsing with PBS, as measured at a load of 3 and 10 grams (corresponding respectively to mean pressures of 0.1 and 0.16 atmospheres).

As shown in FIG. 5, PVP/HSPC liposome and HA/HSPC liposome mixtures resulted in a reduction of 25-30% in the friction coefficients of Etafilcon A lenses in comparison with HSPC liposomes alone at a load of 10 grams.

As further shown in FIGS. 4 and 5, the abovementioned polymer/liposome mixtures resulted in a reduction of about 90% or more in the friction coefficients of Etafilcon A lenses in comparison with PBS or polymer solutions.

Figure 6:
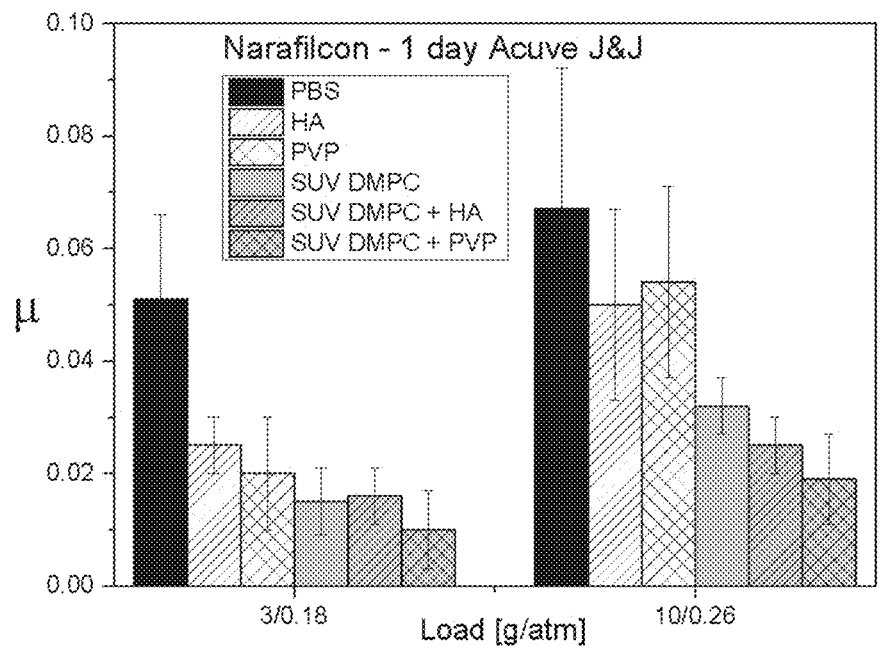
FIG. 6 presents bar graphs showing the friction coefficient of Narafilcon A contact lens upon immersion in PBS, solutions of HA or PVP (0.2 mg/ml), a solution of SUV DMPC liposomes (10 mM), or solutions of SUV DMPC liposomes with HA or PVP, followed by rinsing with PBS, as measured at a load of 3 and 10 grams (corresponding respectively to mean pressures of 0.18 and 0.26 atmospheres).
Figure 7:
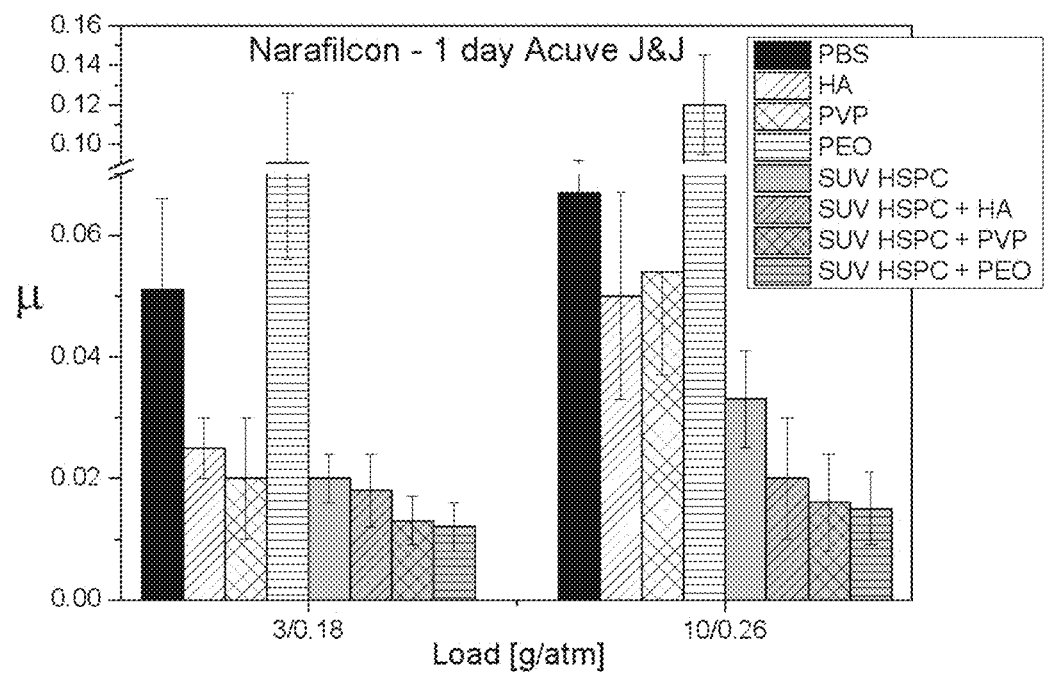
FIG. 7 presents bar graphs showing the friction coefficient of Narafilcon A contact lens upon immersion in PBS, solutions of HA, PVP or PEO (0.2 mg/ml), a solution of SUV HSPC liposomes (10 mM), or solutions of SUV HSPC liposomes with HA, PVP or PEO, followed by rinsing with PBS, as measured at a load of 3 and 10 grams (corresponding respectively to mean pressures of 0.18 and 0.26 atmospheres).

As shown in FIG. 6, PVP/DMPC liposome and HA/DMPC liposome mixtures resulted in a reduction of 22-40% in the friction coefficients of Narafilcon A lenses in comparison with DMPC liposomes alone, and a reduction of 50-72% in comparison with PBS or the respective polymer solutions, at a load of 10 grams.

As shown in FIG. 7, PEO/HSPC liposome, PVP/HSPC liposome and HA/HSPC liposome mixtures resulted in a reduction of 40-54% in the friction coefficients of Narafilcon A lenses in comparison with HSPC liposomes alone, and a reduction of 60-91% in comparison with PBS or the respective polymer solutions, at a load of 10 grams.

As further shown in FIGS. 4-7, mixtures of the non-ionic polar polymers PVP and PEO with liposomes resulted in at least as great a reduction in sliding friction coefficients µ as did immersion in mixtures of the ionic polymer hyaluronic acid with liposomes.

These results indicate that solutions containing ionic or non-ionic water-soluble polymers and the liposomes resulted in friction coefficient values which were substantially lower than the friction coefficient values obtained for either component alone, thus demonstrating a synergistic effect.

These results further indicate that SUV liposomes are highly effective at reducing friction coefficients (as are MLV liposomes described in Example 1) in combination the polar polymers.

As further shown in FIG. 4, a mixture of PEO and DMPC SUVs was particularly effective at reducing sliding friction coefficients of Etafilcon A lenses, whereas PEO alone had no effect on the sliding friction coefficient at a relatively low load (3 grams), and resulted in an increased sliding friction coefficient at a higher load (10 grams).

Similarly, as shown in FIG. 7, a mixture of PEO and HSPC SUVs was particularly effective at reducing sliding friction coefficients of Narafilcon A lenses, whereas PEO alone resulted in increased sliding friction coefficients.

These results surprisingly indicate a particularly strong synergy (at reducing friction coefficients) between PEO (which is not effective at reducing friction coefficients by itself) and liposomes of different types, and on different surfaces.

TABLE 1

Friction coefficients of Etafilcon A and Narafilcon A contact lenses under different loads and mean pressures, following immersion in PBS solution with or without liposomes and/or a polar polymer (hyaluronic acid (HA), polyvinylpyrrolidone (PVP) or polyethylene oxide (PEO)).

| Lens Material | Load (grams) | Mean Pressure (Atm) | Liposome type | Polymer in PBS Solution | | | |
|---|---|---|---|---|---|---|---|
| | | | | No polymer | HA | PVP | PEO |
| Etafilcon A | 3 | 0.1 | No liposomes | 0.21 ± 0.07 | 0.055 ± 0.01 | 0.02 ± 0.005 | 0.2 ± 0.02 |
| | | | DMPC liposomes | 0.015 ± 0.005 | 0.012 ± 0.006 | 0.01 ± 0.005 | 0.009 ± 0.003 |
| | | | HSPC liposomes | 0.016 ± 0.007 | 0.015 ± 0.005 | 0.011 ± 0.003 | N.D. |
| | 10 | 0.16 | No liposomes | 0.28 ± 0.055 | 0.31 ± 0.1 | 0.11 ± 0.03 | 0.45 ± 0.05 |
| | | | DMPC liposomes | 0.024 ± 0.007 | 0.024 ± 0.008 | 0.012 ± 0.004 | 0.009 ± 0.003 |
| | | | HSPC liposomes | 0.024 ± 0.009 | 0.017 ± 0.005 | 0.018 ± 0.003 | N.D. |

TABLE 1-continued

Friction coefficients of Etafilcon A and Narafilcon A contact lenses under different loads and mean pressures, following immersion in PBS solution with or without liposomes and/or a polar polymer (hyaluronic acid (HA), polyvinylpyrrolidone (PVP) or polyethylene oxide (PEO)).

| Lens Material | Load (grams) | Mean Pressure (Atm) | Liposome type | Polymer in PBS Solution | | | |
|---|---|---|---|---|---|---|---|
| | | | | No polymer | HA | PVP | PEO |
| Narafilcon A | 3 | 0.18 | No liposomes | 0.051 ± 0.015 | 0.025 ± 0.005 | 0.02 ± 0.01 | 0.09 ± 0.03 |
| | | | DMPC liposomes | 0.015 ± 0.005 | 0.016 ± 0.005 | 0.01 ± 0.0035 | N.D. |
| | | | HSPC liposomes | 0.02 ± 0.004 | 0.018 ± 0.006 | 0.013 ± 0.004 | 0.012 ± 0.004 |
| | 10 | 0.26 | No liposomes | 0.067 ± 0.025 | 0.05 ± 0.017 | 0.054 ± 0.017 | 0.12 ± 0.028 |
| | | | DMPC liposomes | 0.032 ± 0.005 | 0.025 ± 0.005 | 0.019 ± 0.007 | N.D. |
| | | | HSPC liposomes | 0.033 ± 0.008 | 0.02 ± 0.01 | 0.016 ± 0.008 | 0.015 ± 0.006 |

N.D. = not determined

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of reducing a friction coefficient of a surface of a contact lens, the method comprising rinsing and/or immersing the contact lens in a solution comprising at least one water-soluble polymer, liposomes, and an aqueous carrier, wherein said at least one water-soluble polymer comprises a non-ionic polymer, and an average molecular weight of said at least one water-soluble polymer is in a range of from 3 kDa to 10 MDa, and wherein a concentration of phospholipids of said liposomes in the solution is in a range of from 0.5 mM to 500 mM.

2. The method of claim 1, wherein said contact lens comprises a hydrogel surface.

3. The solution of claim 2, wherein said hydrogel comprises a polymer selected from the group consisting of poly(2-hydroxyethyl methacrylate) and a silicone.

4. The method of claim 2, wherein said hydrogel comprises a silicone.

5. The method of claim 2, wherein said hydrogel comprises a polymer having no more than one negatively charged group per 2 kDa.

6. The method of claim 1, wherein said non-ionic polymer is selected from the group consisting of a polyvinylpyrrolidone and a polyethylene glycol.

7. The method of claim 1, wherein a molar percentage of phosphatidylcholine in said liposomes is at least 50%.

8. The method of claim 1, wherein said liposomes are selected from the group consisting of small unilamellar vesicles, large unilamellar vesicles and multilamellar vesicles.

9. The method of claim 1, wherein said liposomes comprise small unilamellar vesicles.

10. The method of claim 1, wherein a viscosity of the solution is no more than 1000 cP.

11. The method of claim 1, wherein said carrier is an ophthalmically acceptable carrier.

* * * * *